(12) United States Patent
Nixon et al.

(10) Patent No.: US 7,364,869 B2
(45) Date of Patent: Apr. 29, 2008

(54) METHOD OF DETECTING ANTIGEN-SPECIFIC T LYMPHOCYTES

(75) Inventors: Douglas Nixon, San Francisco, CA (US); Barbara Shacklett, Davis, CA (US); Wim Jennes, Antwerpen (BE); Luc Kestens, Antwerpen (BE)

(73) Assignee: The J. David Gladstone Institutes, San Francisco, CA (US)

( * ) Notice: Subject to any disclaimer, the term of this patent is extended or adjusted under 35 U.S.C. 154(b) by 393 days.

(21) Appl. No.: 10/895,239

(22) Filed: Jul. 19, 2004

(65) Prior Publication Data

US 2005/0074822 A1 Apr. 7, 2005

Related U.S. Application Data

(60) Provisional application No. 60/491,225, filed on Jul. 29, 2003.

(51) Int. Cl.
*G01N 33/53* (2006.01)
(52) U.S. Cl. .................. 435/7.24; 435/7.94; 435/375; 435/377
(58) Field of Classification Search .................. None
See application file for complete search history.

(56) References Cited

U.S. PATENT DOCUMENTS

| 5,705,151 A * | 1/1998 | Dow et al. ............... 424/93.21 |
| 6,383,763 B1 | 5/2002 | Wallis |
| 7,169,571 B2 * | 1/2007 | Wier ....................... 435/7.24 |

2003/0195194 A1* 10/2003 Gaeta et al. ................ 514/218

OTHER PUBLICATIONS

Napolitano et al, Nature Medicine, vol. 7, No. 1, 73-79, 2001.*
Brown et al. (2000) *J. Infect. Dis.* 182:1039.
Czerinsky et al. (1983) *J. Immunol. Methods* 65:109.
Czerinsky et al. (1988) *J. Immunol. Methods* 110:29.
Elghazali et al. (1997) *Clin. Exp. Immunol.* 109:84.
Fiorillo et al. (2000) *J. Clin. Invest.* 106:47.
Geginat et al. (2001) *J. Immunol.* 166:1877.
Geginat et al. (2001) *J. Exp. Med.* 194:1711.
Goldrath et al. (2002) *J. Exp. Med.* 195:1515.
Jager et al. (2000) *J. Exp. Med.* 191:625.
Jennes et al. (2002) *J. Immunol. Methods* 270:99-108.
King et al. (1993) *J. Immunol.* 150:1873.
Kouwenhoven et al. (2001) *Clin. Diagn. Lab Immunol.* 8:1248.
Ku et al. (2000) *Science* 288:675.
Larsson et al. (2002) *AIDS* 16:171.
Schmitz et al. (2002) *J. Clin. Lab Anal.* 16:30.
Smith et al. (2000) *J. Immunol.* 165:7088.
Subklewe et al. (1999) *Eur. J. Immunol.* 29:3995.
Tan et al. (1999) *J. Immunol.* 162:1827.
Tan et al. (2002) *J. Exp. Med.* 195:1523.
Reece et al., "Naturally Exposed Populations Differ in Their T1 and T2 Responses to the Circumsporozoite Protein of *Plasmodium falciparum*" *Infection and Immunity* (2002), vol. 70, No. 3, pp. 1468-1474.

* cited by examiner

*Primary Examiner*—David A. Saunders
(74) *Attorney, Agent, or Firm*—Paula A. Borden; Bozicevic, Field & Francis LLP

(57) ABSTRACT

The present invention provides a method of detecting antigen-specific T lymphocytes in a sample. The present invention further provides kits and systems for detecting antigen-specific T lymphocytes in a sample.

13 Claims, 5 Drawing Sheets

α-CD28/α-CD49d

α-CD28/α-CD49d

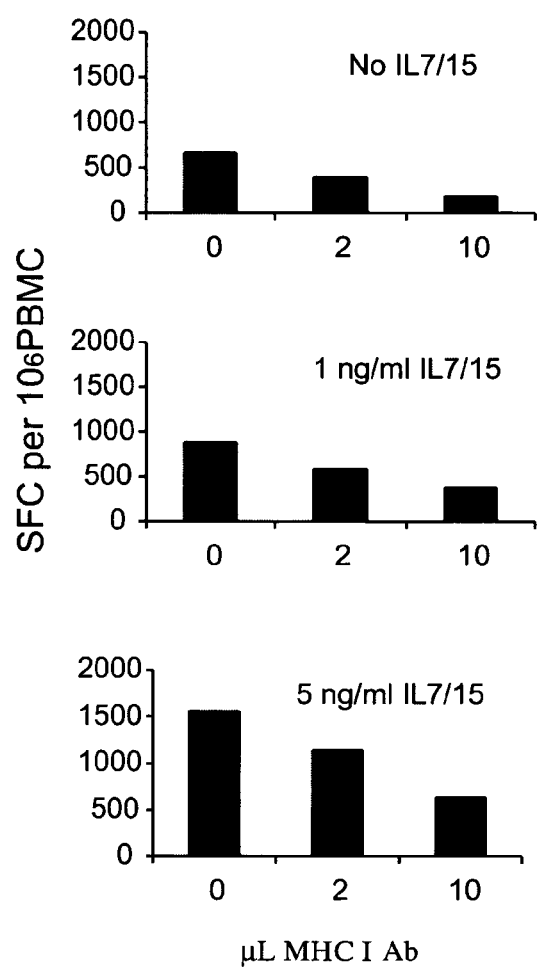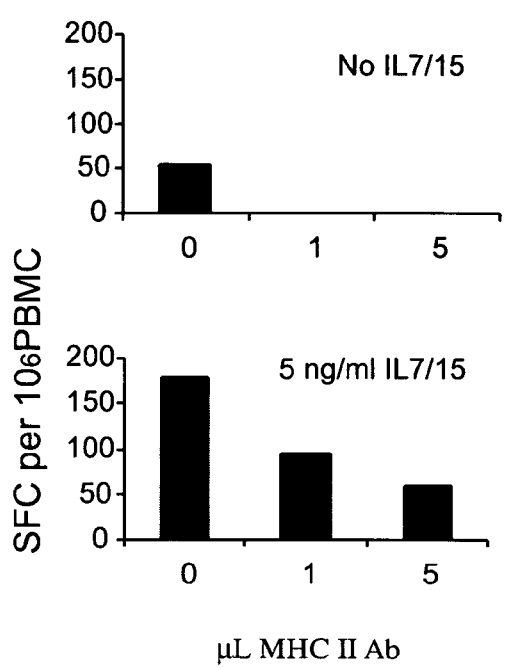
FIG. 5A
FIG. 5B

METHOD OF DETECTING ANTIGEN-SPECIFIC T LYMPHOCYTES

CROSS-REFERENCE

This application claims the benefit of U.S. Provisional Patent Application No. 60/491,225 filed Jul. 29, 2003, which application is incorporated herein by reference in its entirety.

STATEMENT REGARDING FEDERALLY SPONSORED RESEARCH

The U.S. government may have certain rights in this invention, pursuant to grant nos. R21-AI47746 and R01-AI46254 awarded by the National Institutes of Health.

FIELD OF THE INVENTION

The present invention is in the field of assays for detecting antigen-specific T cells.

BACKGROUND OF THE INVENTION

The enzyme linked immunosorbent spot (ELISPOT) assay has become widely utilized as a tool to study cellular and humoral immune responses in vitro. ELISPOT has been used to determine the frequency of specific $CD4^+$ and $CD8^+$ T cell responses to self, tumor, viral, bacterial and other antigens. Secretion of a range of cytokines (IFN-γ, TGF-β, TNF-α, IL-4, IL-5, IL-6, IL-10, IL-12), β-chemokines (MIP-1α, MIP-1β, RANTES) and cytotoxins (granzymes) may be measured. The sensitivity of the ELISPOT assay for detecting $CD8^+$ T cell responses has been estimated to be at least 1 $\log_{10}$ higher than traditional limiting dilution analysis or bulk $^{51}Cr$ release assay.

Use of autologous dendritic cells as antigen-presenting cells may augment the sensitivity of ELISPOT. However, this method requires large amounts of fresh peripheral blood and in vitro maturation of monocytes over a period of 5 to 7 days. Thus, although the sensitivity and technical ease of the ELISPOT assay make it a useful alternative to traditional analytical methods, there remains a need for increased sensitivity in detection of low frequency antigen-specific T cell responses. The present invention addresses this need.

Literature

Czerkinsky et al. (1983) *J. Immunol. Methods* 65:109; Czerkinsky et al. (1988) *J. Immunol. Methods* 110:29; Fiorillo et al. (2000) *J. Clin. Invest.* 106:47; Pelfrey et al. (2000) *J. Immunol.* 165:1641; Jager et al. (2000) *J. Exp. Med.* 191:625; Nagorsen et al. (2000) *Cancer Res.* 60:4850; Larsson et al. (1999) *AIDS* 13:767; Tan et al. (1999) *J. Immunol.* 162:1827; Brown et al. (2000) *J. Infect. Dis.* 182:1039; Smith et al. (2000) *J. Immunol.* 165:7088; Geginat et al. (2001) *J. Immunol.* 166:1877; King et al. (1993) *J. Immunol.* 150:1873; Elghazali et al. (1997) *Clin. Exp. Immunol.* 109:84; Ozenci et al. (2000) *Cytokine* 12:1218; Kouwenhoven et al. (2001) *Clin. Diagn. Lab Immunol.* 8:1248; Ostrowski et al. (2001) *J. Infect. Dis.* 184:1268; Reece et al. (2002) *Infect. Immun.* 70:1468; Rininsland et al. (2000) *J. Immunol. Methods* 240:143; Miyahira et al. (1995) *J. Immunol. Methods* 181:45; Murali-Krishna et al. (1998) *Immunity* 8:177; Larsson et al. (2002) *AIDS* 16:171; Subklewe et al. (1999) *Eur. J. Immunol.* 29:3995; Schmitz et al. (2002) *J. Clin. Lab Anal.* 16:30; Lau et al. (1994) *Nature* 369:648; Nakajima et al. (1997) *Nat. Med.* 7:73; Ku et al. (2000) *Science* 288:675; Schluns et al. (2000) *Nat. Immunol.* 1:426; Geginat et al. (2001) *J. Exp. Med.* 194:1711; Goldrath et al. (2002) *J. Exp. Med.* 195:1515; Tan et al. (2002) *J. Exp. Med.* 195:1523; Jennes et al. (2002) *J. Immunol. Methods* 270:99-108; U.S. Pat. No. 6,383,763.

SUMMARY OF THE INVENTION

The present invention provides a method of detecting antigen-specific T lymphocytes in a sample. The present invention further provides kits and systems for detecting antigen-specific T lymphocytes in a sample.

BRIEF DESCRIPTION OF THE DRAWINGS

FIGS. 5A and 5B depict modification of the assay by inhibition of $CD8^+$ responses (FIG. 5A) and $CD4^+$ responses (FIG. 5B).

DEFINITIONS

Figure 1A:
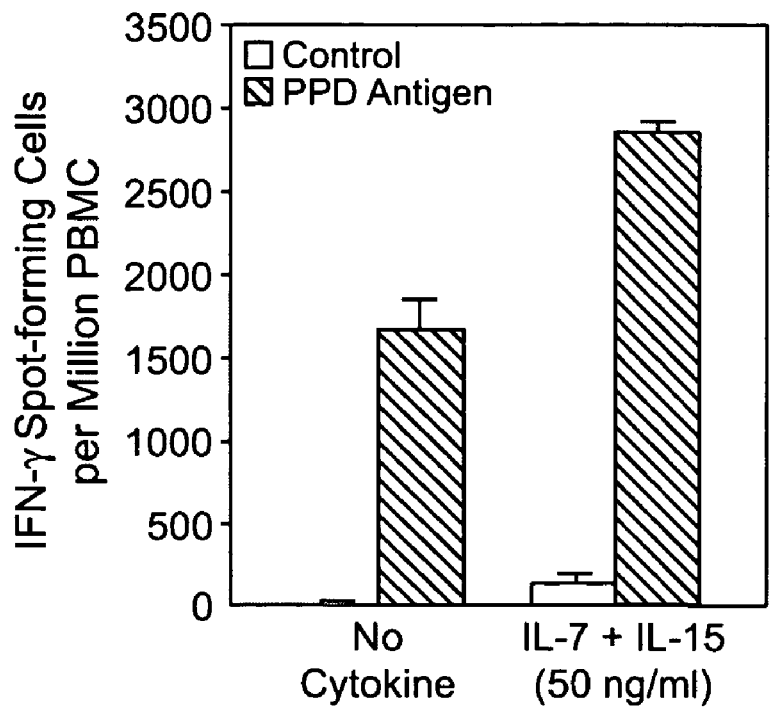
FIGS. 1A and 1B depict ELISPOT detection of PPD-specific CD4+ T cell responses in fresh and cryopreserved PBMC from donor 1 with addition of both IL-7 and IL-15.

The terms "individual," "host," "subject," and "patient," used interchangeably herein, refer to a mammal, particularly a human. Other subjects of interest can include mammalian domesticated animals (cats, dogs, horses, etc.), mammalian farm animals (cows, goats, sheep, etc.), rodents, and the like.

As used herein, a "biological sample" is a sample that comprises one or more antigen-specific T lymphocytes. As such, the term "biological sample" is used interchangeably herein with "cell sample." A "biological sample" encompasses a variety of sample types obtained from an individual and can be used in a subject diagnostic or monitoring assay. A biological sample encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents (e.g., heparinization of blood samples); washed; or enrichment for certain cell populations, such as $CD4^+$ T lymphocytes, $CD8^+$ T lymphocytes, glial cells, macrophages, tumor cells, peripheral blood mononuclear cells (PBMC), and the like. The term "biological sample" encompasses a clinical sample, and also includes cells in culture, cell supernatants, tissue samples, organs, bone marrow, and the like. The term "biological sample" also includes preserved samples, including cryopreserved tissues, cryopreserved cell samples, and the like.

As used herein, the terms "interleukin-15 receptor," "IL-15 receptor," and "IL-15R" refer to proteins that are present on the cell surface and that specifically bind IL-15. The IL-15 receptor typically is a heterotrimeric complex that includes an IL-2β chain, an IL-2γ chain, and a unique IL-15α chain. See, e.g., U.S. Pat. No. 6,548,065; and GenBank Accession Nos. NP_751950, NP_598597, and NP_032384; and GenBank Accession Nos. NM_002189, NM_172200, and NM_133836. The term "IL-15 receptor agonist" refers to a compound that binds to and activates an IL-15 receptor.

As used herein, the terms "interleukin-7 receptor," "IL-7 receptor," and "IL-7R" refer to proteins that are present on the cell surface and specifically bind IL-7. The IL-7 receptor alpha chain is described in the literature. See, e.g., Goodwin et al. (1990) Cell 60:941-951; GenBank Accession Nos. NP_032398 and NP_002176. IL-7R is also referred to in the literature as CD127. The term "IL-7 receptor agonist" refers to a compound that binds to and activates an IL-7 receptor.

The terms "antigen" and "epitope" are well understood in the art and refer to the portion of a macromolecule which is specifically recognized by a component of the immune system, e.g., an antibody or a T-cell antigen receptor. As used herein, the term "antigen" encompasses antigenic epitopes, e.g., fragments of an antigen which are antigenic epitopes. Epitopes are recognized by antibodies in solution, e.g. free from other molecules. Epitopes are recognized by T-cell antigen receptor when the epitope is associated with a class I or class II major histocompatibility complex molecule.

"An antigen associated with a pathogenic organism," as used herein, is a polypeptide (or fragment or analog thereof) that is normally a part of a pathogenic organism, or is produced by a pathogenic organism. An antigen associated with a pathogenic organism is in some embodiments isolated from a naturally-occurring pathogenic organism. An antigen associated with a pathogenic organism is in some embodiments a synthetic polypeptide (e.g., a polypeptide generated in a laboratory using standard methods of in vitro peptide synthesis) or recombinantly produced polypeptide that shares at least one epitope with a naturally-occurring antigen associated with a pathogenic organism.

The term "tumor-associated antigen" is a term well understood in the art, and refers to surface molecules that are differentially expressed in tumor cells relative to non-cancerous cells of the same cell type. As used herein, "tumor-associated antigen" includes not only complete tumor-associated antigens, but also epitope-comprising portions (fragments) thereof. A tumor-associated antigen (TAA) may be one found in nature, or may be a synthetic version of a TAA found in nature, or may be a variant of a naturally-occurring TAA, e.g., a variant which has enhanced immunogenic properties.

An "allergen" as used herein refers to a molecule capable of provoking an immune response characterized by production of IgE. Thus, in the context of this invention, the term "allergen" refers to an antigen which triggers, in an individual who is susceptible to such (e.g., an individual who has been sensitized to the antigen), an allergic response which is mediated by IgE antibody. "Allergens" include fragments of allergens and haptens that function as allergens.

As used herein the term "isolated" is meant to describe a compound of interest (e.g., an antigen) that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is substantially free from other components with which it is naturally associated, e.g., is at least 60% pure, at least 75% pure, at 90% pure, at least 95% pure, at least 98% pure, or at least 99% pure.

The terms "CD4$^+$-deficient" and "CD4$^+$-low" are used interchangeably herein, and, as used herein, refer to a state of an individual in whom the number of CD4$^+$T lymphocytes is reduced compared to an individual with a healthy, intact immune system. CD4$^+$ deficiency includes a state in which the number of functional CD4$^+$T lymphocytes is less than about 600 CD4$^+$T cells/mm$^3$ blood; a state in which the number of functional CD4$^+$T cells is reduced compared to a healthy, normal state for a given individual; and a state in which functional CD4$^+$ T cells are completely absent.

As used herein, a "CD4$^+$-deficient individual" is one who has a reduced number of functional CD4$^+$-T cells, regardless of the reason, when compared to an individual having a normal, intact immune system. In general, the number of functional CD4$^+$-T cells that is within a normal range is known for various mammalian species. In human blood, e.g., the number of functional CD4$^+$-T cells which is considered to be in a normal range is from about 600 to about 1500 CD4$^+$-T cells/mm$^3$ blood. An individual having a number of CD4$^+$-T cells below the normal range, e.g., below about 600/mm$^3$, may be considered "CD4$^+$-deficient." Thus, a CD4$^+$-deficient individual may have a low CD4$^+$ T cell count, or even no detectable CD4$^+$ T cells. A CD4$^+$-deficient individual includes an individual who has a lower than normal number of functional CD4+-T cells due to a primary or an acquired immunodeficiency.

As used herein, the terms "solid support" and "insoluble support" are used interchangeably to refer to any solid material to which reagents such as antibodies, antigens, and other compounds may be attached. For example, in an enzyme linked immunosorbent assay (ELISA) method, the wells of microtiter plates often provide solid supports. Other examples of solid supports include microscope slides, coverslips, test strips, beads, particles, cell culture flasks, as well as many other items.

The term "binds specifically," in the context of antibody binding, refers to high avidity and/or high affinity binding of an antibody to a specific polypeptide i.e., epitope of a polypeptide, e.g., a CD4 polypeptide, a CD8 polypeptide, a secreted factor, and the like. For example, antibody binding to an epitope on a factor secreted by an antigen-specific T lymphocyte is stronger than binding of the same antibody to any other epitope, particularly those which may be present in molecules in association with, or in the same sample, as the specific polypeptide of interest, e.g., binds more strongly to a specific secreted factor epitope than to any other polypeptide so that by adjusting binding conditions the antibody binds almost exclusively to the specific secreted factor epitope and not to any other polypeptide, or to any other polypeptide which does not comprise the epitope exhibited by the secreted factor. Antibodies which bind specifically to a polypeptide may be capable of binding other polypeptides at a weak, yet detectable, level (e.g., 10% or less of the binding shown to the polypeptide of interest). Such weak binding, or background binding, is readily discernible from the specific antibody binding to a particular polypeptide, e.g. by use of appropriate controls. In general, specific antibodies bind to a given polypeptide with a binding affinity of $10^{-7}$ M or more, e.g., $10^{-8}$ M or more (e.g., $10^{-9}$ M, $10^{-10}$ M, $10^{-11}$ M, etc.). In general, an antibody with a binding affinity of $10^{-6}$ M or less is not useful in that it will not bind an antigen at a detectable level using conventional methodology currently used.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a T lymphocyte" includes a plurality of such lymphocytes and reference to "the agonist" includes reference to one or more agonists and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides a method of detecting antigen-specific T lymphocytes in a sample. The present invention further provides kits and systems for detecting antigen-specific T lymphocytes in a sample.

The invention is based in part on the observation that the sensitivity of detecting antigen-specific T lymphocytes is significantly augmented by contacting a sample containing T lymphocytes with the cytokines interleukin-7 (IL-7) and interleukin-15 (IL-15). The present invention provides a method of detecting antigen-specific T lymphocytes in a sample, where the limits of detection are lower than previously attainable.

Methods of Detecting Antigen-Specific T Lymphocytes

The present invention provides methods of detecting antigen-specific T lymphocytes in a cell sample that comprises an antigen-specific T lymphocyte. The methods generally involve contacting a cell sample with antigen, an IL-7 receptor agonist, and an IL-15 receptor agonist, forming a test sample; and detecting an antigen-specific T lymphocyte in the test sample, e.g., detecting a T lymphocyte in a biological sample that is specific for the antigen in the test sample.

Using a subject method, an antigen-specific T lymphocyte is detected in a cell sample (e.g., a biological sample that comprises cells) that may comprise an antigen-specific T lymphocyte, and may further comprise cells other than the antigen-specific T lymphocyte that is being detected, e.g., other cell types and/or T lymphocytes that are not antigen specific and/or T lymphocytes that are antigen specific but are specific for an antigen other than the antigen to which the T lymphocyte being detected is specific. Using a subject method, an antigen-specific T lymphocyte is detected at a concentration of from about 1 antigen-specific T lymphocyte per $10^3$ cells to about 1 antigen-specific T lymphocyte per $10^7$ cells other than the antigen-specific T lymphocyte that is being detected, e.g., from about 1 antigen-specific T lymphocyte per 10 cells to about 1 antigen-specific T lymphocyte per $10^4$ cells, from about 1 antigen-specific T lymphocyte per $10^4$ cells to about 1 antigen-specific T lymphocyte per $10^5$ cells, from about 1 antigen-specific T lymphocyte per $10^5$ cells to about 1 antigen-specific T lymphocyte per $10^6$ cells, from about 1 antigen-specific T lymphocyte per $10^6$ cells to about 1 antigen-specific T lymphocyte per $5\times10^6$ cells, or from about 1 antigen-specific T lymphocyte per $5\times10^6$ cells to about 1 antigen-specific T lymphocyte per $10^7$ cells other than the antigen-specific T lymphocyte that is being detected.

Using a subject method, detection of an antigen-specific T lymphocyte in a cell sample containing cells other than the antigen-specific T lymphocyte that is being detected is enhanced by from about 2-fold to about 100-fold, or more, compared to detection in the absence of a IL-15 receptor agonist and an IL-7 receptor agonist. Thus, e.g., the level of a detectable marker produced by an antigen-specific T lymphocyte in the presence of an IL-1SR agonist and an IL-7R agonist is increased by from about 2-fold to about 5-fold, from about 5-fold to about 10-fold, from about 10-fold to about 15-fold, from about 15-fold to about 20-fold, from about 20-fold to about 25-fold, from about 25-fold to about 30-fold, from about 30-fold to about 40-fold, from about 40-fold to about 50-fold, from about 50-fold to about 60-fold, from about 60-fold to about 70-fold, from about 70-fold to about 80-fold, from about 80-fold to about 90-fold, or from about 90-fold to about 100-fold, or more, compared to the level of the detectable marker produced in the absence of an IL-15R agonist and an IL-7R agonist.

A detectable marker (e.g., a molecule that is produced and/or secreted by an antigen-specific T lymphocyte in response to signaling via the T cell antigen receptor), e.g., a secreted factor, a cell-surface marker, etc., that is produced by an antigen-specific T lymphocyte includes, but is not limited to, a cell-surface molecule such as a T cell antigen receptor (TCR); and secreted factors such as IFN-γ, IL-2, IL-4, IL-10, TNF-α, MIP-1α, MIP-1β, RANTES, a granzyme, and perforin. In some embodiments, two or more such detectable markers are detected in a single assay.

A subject method generally involves contacting a cell sample that is being tested for the presence of an antigen-specific T lymphocyte with an antigen, an IL-15R agonist, and an IL-7R agonist, forming a test sample. A "test sample" thus includes a cell sample (e.g., a biological sample comprising cells), an antigen, an IL-15R agonist, and an IL-7R agonist.

The amount of antigen included in the test sample will vary, but will generally be in the range of from about 0.1 μg/ml to about 50 μg/ml, e.g., from about 0.1 μg/ml to about 0.5 μg/ml, from about 0.5 μg/ml to about 1 μg/ml, from about 1 μg/ml to about 2.5 μg/ml, from about 2.5 μg/ml to about 5 μg/ml, from about 5 μg/ml to about 10 μg/ml, from about 10 μg/ml to about 20 μg/ml, from about 20 μg/ml to about 30 μg/ml, from about 30 μg/ml to about 40 μg/ml, or from about 40 μg/ml to about 50 μg/ml.

In many embodiments, the antigen in the test sample will be an isolated antigen, e.g., an antigen that is separated from other components (e.g., other macromolecules) with which it is found in nature. In many embodiments, the antigen in the test sample is a purified antigen, e.g., an antigen that is from about 80% to about 90%, from about 90% to about 95%, from about 95% to about 98%, from about 98% to about 99%, or from about 99% to about 100% pure. In many embodiments, the antigen in the test sample will be a synthetic antigen, e.g., produced by standard methods for synthesizing proteins. In many embodiments, the antigen will be a human leukocyte antigen (HLA)-restricted antigen. Typically, the antigen comprises one or more T-cell epitopes. The antigen is in many embodiments presented by an antigen-presenting cell (APC) present in the biological sample.

The amount of IL-15R agonist and the amount of IL-7R agonist may vary, but will generally be in the range of from about 1 ng/ml to about 100 ng/ml, e.g., from about 1 ng/ml to about 5 ng/ml, from about 5 ng/ml to about 10 ng/ml, from about 10 ng/ml to about 20 ng/ml, from about 20 ng/ml to about 30 ng/ml, from about 30 ng/ml to about 40 ng/ml, from about 40 ng/ml to about 50 ng/ml, from about 50 ng/ml to about 60 ng/ml, from about 60 ng/ml to about 70 ng/ml, from about 70 ng/ml to about 80 ng/ml, from about 80 ng/ml to about 90 ng/ml, or from about 90 ng/ml to about 100 ng/ml.

In general, the test sample (including cells, an antigen, an IL-15R agonist, and an IL-7R agonist) will be kept for a suitable period of time under conditions that permit an increase in a signal (e.g., a cell surface marker or a secreted factor) produced by an antigen-specific T lymphocyte. Typically, "suitable conditions" include incubation at 37° C. in an atmosphere including 5% $CO_2$, although other suitable conditions are readily envisioned by those skilled in the art (e.g., where the incubation temperature varies from 37° C. by one or more degrees Celsius). A "suitable period of time," is generally from about 15 minutes to about 20 hours, e.g., from about 15 minutes to about 30 minutes, from about 30 minutes to about 1 hour, from about 1 hour to about 4 hours, from about 4 hours to about 8 hours, from about 8 hours to about 12 hours, from about 12 hours to about 16 hours, or from about 16 hours to about 20 hours. Shorter or longer periods of time are also contemplated.

Detection of antigen-specific T lymphocytes can be qualitative or quantitative. In some embodiments, the detection is qualitative, e.g., the result is either expressed as "antigen-specific T lymphocytes detected in sample" or "no antigen-specific T lymphocytes detected in sample." In other embodiments, the detection is quantitative. In these embodiments, a level of antigen-specific T lymphocytes is determined. Detection of the level of antigen-specific T lymphocytes in a sample is useful in methods for monitoring the efficacy of a given therapeutic regimen; in staging a disorder (e.g., monitoring the progression of the disorder); and in clinical studies, e.g., for comparing the level of antigen-specific T lymphocyte from individual to individual, or in an individual over time.

Antigen-specific T lymphocytes include $CD4^+$ T lymphocytes and $CD8^+$ T lymphocytes. In some embodiments, a subject method further includes a step that allows discrimination between $CD4^+$ T lymphocytes and $CD8^+$ T lymphocytes. Reduction in the number and/or detection of $CD8^+$ T lymphocytes increases the level and/or specificity of detection of an antigen-specific $CD4^+$ T lymphocyte. Reduction in the number and/or detection of $CD4^+$ T lymphocytes increases the level and/or specificity of detection of an antigen-specific $CD8^+$ T lymphocyte. In some of these embodiments, a subject method includes reducing the number of $CD4^+$ T lymphocytes and/or reducing detection of $CD4^+$ T lymphocytes in the cell sample being tested, thereby increasing the level and/or specificity of detection of an antigen-specific $CD8^+$ lymphocyte. In other of these embodiments, a subject method further includes reducing the number of $CD8^+$ T lymphocytes and/or detection of $CD8^+$ T lymphocytes in the cell sample being tested, thereby increasing the level and/or specificity of detection of an antigen-specific $CD4^+$ T lymphocyte.

Where the method includes reducing the number of $CD4^+$ T lymphocytes and/or reducing detection of $CD4^+$ T lymphocytes in the cell sample, the number of $CD4^+$ T lymphocytes and/or detection of $CD4^+$ T lymphocytes can be reduced using any known method. As one non-limiting example, a subject method is carried out in the presence of an MHC Class II blocking antibody, such that $CD4^+$ T lymphocytes are not activated and therefore are not detected. For example, a test sample includes a cell sample, an IL-15R agonist, an IL-7R agonist, and an antibody that binds to an MHC Class II polypeptide (e.g., an antibody specific for a MHC Class II polypeptide). Methods of reducing the number of $CD4^+$ T lymphocytes in a sample include removing $CD4^+$ T lymphocytes from a cell sample using antibody to a CD4 molecule immobilized on a solid support, e.g., a magnetic bead; use of antibody to $CD4^+$ T lymphocytes and complement to lyse $CD4^+$ T lymphocytes; and the like. As one non-limiting example, a subject method is carried out in the presence of an antibody that binds CD4 (e.g., an antibody specific for a CD4 polypeptide). The anti-CD4 antibody will in some embodiments be an antibody that inhibits antigen-induced activation of $CD4^+$ cells without lysing the cells. The anti-CD4 antibody will in other embodiments result in lysis of the $CD4^+$ T cells. For example, complement is added along with the anti-CD4 antibody, and $CD4^+$ T cells are lysed. In other embodiments, the anti-CD4 antibody is used to remove $CD4^+$ T cells from the sample. For example, an anti-CD4 antibody is immobilized onto a magnetic bead, $CD4^+$ T lymphocytes adhere to the immobilized anti-CD4 antibody, and the adhered $CD4^+$ T lymphocytes are removed. In some embodiments, more than one anti-CD4 antibody is used.

Where the method includes reducing the number of $CD8^+$ T lymphocytes and/or reducing detection of $CD8^+$ T lymphocytes in the cell sample, the number of $CD8^+$ T lymphocytes and/or detection of $CD8^+$ T lymphocytes can be reduced using any known method. As one non-limiting example, a subject method is carried out in the presence of an MHC Class I blocking antibody (e.g., an antibody specific for an MHC Class I polypeptide), such that $CD8^+$ T lymphocytes are not activated and therefore are not detected. For example, a test sample includes a cell sample, an IL-15R agonist, an IL-7R agonist, and an antibody that binds to an MHC Class I polypeptide. Other methods of reducing the number of CD8+ T lymphocytes in a sample include removing CD8+ T lymphocytes from a cell sample using antibody to a CD8 molecule immobilized on a solid support, e.g., a magnetic bead; use of antibody to CD8+ T lymphocytes and complement to lyse CD8+ T lymphocytes; and the like. As another non-limiting example, a subject method is carried out in the presence of an antibody that binds CD8 (e.g., an antibody specific for CD8). The anti-CD8 antibody will in some embodiments be an antibody that inhibits antigen-induced activation of CD8+ cells without lysing the cells. The anti-CD8 antibody will in other embodiments result in lysis of the CD8+ T cells. For example, complement is added along with the anti-CD8 antibody, and CD8+ T cells are lysed. In other embodiments, the anti-CD8 antibody is used to remove CD8+ T cells from the sample. For example, an anti-CD8 antibody is immobilized onto a magnetic bead, CD8+ T lymphocytes adhere to the immobilized anti-CD8 antibody, and the adhered CD8+ T lymphocytes are removed. In some embodiments, more than one anti-CD8 antibody is used.

In some embodiments, a subject method will further include a step to determine whether an antigen-specific T cell detected by a subject method is an effector T cell or a memory T cell. Such a step involves the use of one or more antibodies that permit discrimination between effector T cells and memory T cells. CD27 is a marker of T cell activation. Use of an antibody to CD27 will in some embodiments be included in a subject method, to allow detection of activated T cells. CD45RA/CD45RO is a marker of memory T cells. Use of an antibody to CD45RA/CD45RO will in some embodiments be included in a subject method, to allow detection of memory T cells. Other methods of discriminating between effector T cells and memory T cells include detecting a level of CCR7 and/or a level of CD62L. High expression of CCR7 and CD62L is indicative of a memory T cell; low expression of CCR7 and CD62L is indicative of an effector T cell. See, e.g., Wherry and Ahmed (2004) *J. Virol.* 78:5535-5545.

Detecting Antigen-specific T Lymphocytes

Any of a variety of methods can be used to detect an antigen-specific T lymphocyte in a sample containing cells other than the antigen-specific T lymphocyte that is being detected. In some embodiments, the antigen-specific T lymphocyte is detected by detecting a level of a secreted factor produced by an antigen-specific T lymphocyte. A detectable factor (e.g., a molecule that is produced and/or secreted by an antigen-specific T lymphocyte in response to signaling via the T cell antigen receptor), e.g., a secreted factor, a cell-surface marker, etc., that is produced by an antigen-specific T lymphocyte includes, but is not limited to, a cell-surface molecule such as a T cell antigen receptor (TCR); and secreted factors such as IFN-γ, IL-2, IL-4, IL-10, TNF-α, MIP-1α, MIP-1β, RANTES, a granzyme, and perforin. In some embodiments, two or more such detectable markers are detected in a single assay. In some of these embodiments, the secreted factor is IFN-γ. In other embodiments, the antigen-specific T lymphocyte is detected by detecting a level of a cell surface marker, e.g., an antigen-specific T-cell receptor (TCR).

In those embodiments in which a secreted factor is detected, the method of detection will generally be an immunological assay for detecting specific antibody-antigen interactions, e.g., an enzyme-linked immunosorbent assay (ELISA), an enzyme linked immunosorbent spot (ELISPOT) assay, an intracellular staining (ICS) assay; and the like.

In many embodiments, a capture agent that binds the secreted factor is immobilized onto an insoluble support. Suitable capture agents include, but are not limited to, a cytokine binding reagent, such as a capture antibody specific for the cytokine to be detected. The captured secreted factor (e.g., a cytokine such as IFN-γ) is visualized by a detection reagent. In some embodiments, the detection reagent is a second cytokine binding reagent (e.g., a second antibody specific for the captured factor) free in solution that is conjugated to enzyme that produces a detectable product upon acting on an appropriate substrate. In other embodiments, the detection reagents is directly labeled, e.g., with a fluorochrome or other detectable moiety, with colored beads, or a ligand such as biotin that can be detected with tertiary reagent that is labeled as above (with a fluorochrome, bead or enzyme).

In some embodiments, two or more different capture reagents are employed, each of which captures a different secreted factor. In these embodiments, each different secreted factor will be detected with a different detection agent, each of which produces a distinguishable detectable signal.

Suitable insoluble supports include, but are not limited to, insoluble supports comprising various materials or combinations of materials including, but not limited to, nitrocellulose, a hydrophobic, PVDF-based material, a hydrophobic, nylon-based material, silicon dioxide, glass, various plastics such as polycarbonate, polystyrene, polypropylene, and the like. Insoluble supports are provided in any of a variety of configurations, including, but not limited to, test strips, multi-well plates, membranes, and the like.

A variety of methods to detect specific antibody-antigen interactions are known in the art and can be used in the method, including, but not limited to, standard immunohistological methods, immunoprecipitation, an enzyme immunoassay, and a radioimmunoassay. In general, the secreted factor-specific antibody will be detectably labeled, either directly or indirectly. Direct labels include radioisotopes; enzymes whose products are detectable (e.g., luciferase, β-galactosidase, horse radish perodixase, alkaline phosphatase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin; fluorescent proteins, e.g., a green fluorescent protein; other fluorogenic and/or chromogenic proteins, e.g., any of a variety of fluorescent and colored proteins from Anthozoan species, as described in, e.g., Matz et al. (1999) *Nature Biotechnol.* 17:969-973; and the like.

The capture reagent (e.g., antibody) may be attached (coupled) to an insoluble support, such as a polystyrene plate or a bead. Indirect labels include second antibodies specific for secreted factor-specific antibodies, wherein the second antibody is labeled as described above; and members of specific binding pairs, e.g., biotin-avidin, and the like. The biological sample may be brought into contact with an immobilized on a solid support or carrier, such as nitrocellulose, that is capable of immobilizing cells, cell particles, or soluble proteins. The support may then be washed with suitable buffers, followed by contacting with a detectably-labeled secreted factor-specific antibody. Detection methods are known in the art and will be chosen as appropriate to the signal emitted by the detectable label. Detection is generally accomplished in comparison to suitable controls, and to appropriate standards.

For example, an antibody, or other specific binding partner for the secreted factor, that is coated onto an insoluble support is used to bind and capture the secreted factor; and cell supernatant is contacted with the antibody or other specific binding partner. The captured secreted factor is detected using a detectably labeled antibody or other specific binding partner.

In some embodiments, the assay is an ELISPOT assay. In these embodiments, an antibody is immobilized on an insoluble support, e.g., a well of a 96-well nitrocellulose plate. To the well is added antigen, IL-15R agonist, IL-7R agonist, and a sample containing cells, forming a test sample. The test sample is kept under appropriate conditions that permit synthesis of secreted factor(s) by an antigen-specific T lymphocyte. Suitable conditions are known to those skilled in the art, and are generally 37° C. in an atmosphere containing 5% $CO_2$. After a suitable time, e.g., from about 15 minutes to about 20 hours, e.g., from about 15 minutes to about 30 minutes, from about 30 minutes to about 1 hour, from about 1 hour to about 4 hours, from about 4 hours to about 8 hours, from about 8 hours to about 12 hours, from about 12 hours to about 16 hours, or from about 16 hours to about 20 hours, the level of secreted factor that has been secreted by the cells and captured by the immobilized antibody is detected, as described above.

In those embodiments involving detection of a cell-surface marker such as an antigen-specific TCR, any of a variety of methods can be used to detect a T lymphocyte bearing on its surface a TCR specific for a given antigen. As one non-limiting example, a fluorescence-activated cell sorting (FACS) method can be used.

Antigens

Antigens include antigens and antigen fragments, including one or more epitopes, that are recognized by T lymphocytes, e.g., T cell epitopes. Antigens include naturally-occurring antigens; synthetic antigens; and recombinant antigens.

Antigens include, but are not limited to, allergens, antigens associated with a pathogenic microorganism, autoantigens, and tumor-associated antigens. Pathogenic microorganisms include, but are not limited to, pathogenic bacteria, viruses, fungi, and parasites (e.g. protozoans such as Trypanosomes, schistosomes, and the like). The antigen may be a naturally-occurring polypeptide or other macromolecule; a synthetic analog of a naturally-occurring polypeptide antigen; a peptoids corresponding to a naturally-occurring polypeptide antigen; and the like. For example, the antigen may be a naturally-occurring polypeptide or other macromolecule associated with a tumor or with a pathogenic organism; a synthetic analog of a naturally-occurring polypeptide associated with a tumor or with a pathogenic organism; or a peptoid corresponding to a naturally-occurring polypeptide associated with a tumor or with a pathogenic organism. Peptoid compounds and methods for their preparation are described in WO 91/19735.

Recombinant antigens include polypeptides that are expressed by recombinant microorganisms. In some embodiments, a recombinant antigen is encoded by a recombinant virus, e.g., a recombinant poxvirus (e.g., vaccinia, canarypox, modified vaccinia virus Ankara). See, e.g., Larsson et al. (1999) *AIDS* 13:767; U.S. Pat. No. 6,576,757.

Where the antigen is a polypeptide antigen, the antigen is in many embodiments a polypeptide of from about 4 to about 50 amino acids in length, e.g., from about 4 amino acids to about 7 amino acids, from about 7 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, or from about 40 amino acids to about 50 amino acids in length.

Allergens

An "allergen" refers to a substance that can induce an allergic response in a susceptible subject. Allergens include, but are not limited to, pollens, insect venoms, animal dander dust, fungal spores and drugs (e.g. penicillin). As used herein, "allergen" encompasses purified allergen, allergenic fragments of an allergen, extracts from a source of allergen, and the like. Allergens of interest include food allergens, chemical allergens (e.g., drugs, cosmetics, and the like), plant-derived allergens, and animal-derived allergens.

Allergens of interest according to the present invention include antigens found in foods such as fruits (e.g., melons, strawberries, pineapple and other tropical fruits), peanuts, peanut oil, other nuts, milk proteins, egg whites, shellfish, tomatoes, etc.; airborne antigens such as grass pollens, animal danders, house mite feces, etc.; drug antigens such as penicillins and related antibiotics, sulfa drugs, barbiturates, anticonvulsants, insulin preparations (particularly from animal sources of insulin), local anesthetics (e.g., Novocain), and iodine (found in many X-ray contrast dyes); insect venoms and agents responsible for allergic dermatitis caused by blood sucking arthropods such as Diptera, including mosquitos (*Anopheles* sp., *Aedes* sp., *Culiseta* sp., *Culex* sp.), flies (*Phlebotomus* sp., *Culicoides* sp.) particularly black flies, deer flies and biting midges, ticks (*Dermmacenter* sp., *Omithodoros* sp., *Otobius* sp.), fleas (e.g., the order *Siphonaptera*, including the genera *Xenopsylla, Pulex* and *Ctenocephalides felis felis*); and latex. The specific allergen may be any type of chemical compound such as, for example, a polysaccharide, a fatty acid moiety, a protein, etc. Antigen preparations may be prepared by any available technique including, for example, isolation from natural sources, in vivo or in vitro expression of recombinant DNA molecules (see, for example, Zeiler et al. (1997) J. Allergy Clin. Immunol. 100(6 Pt 1):721-727, chemical synthesis, or other technique known in the art.

A wide variety of allergen preparations are available in the art, and many allergens have been molecularly cloned. For example, cloned allergens include *Dermatophagoides pteryonyssinus* (Der P1); Lol pl-V from rye grass pollen; various insect venoms including venom from jumper ant *Myrmecia pilosula*, *Apis mellifera* bee venom phospholipase A2 ($PLA_2$) and antigen 5S, phospholipases from the yellow jacket Vespula maculifrons and white faced hornet *Dolichovespula maculata*; a large number of pollen proteins including birch pollen, ragweed pollen, Parol (the major allergen of *Parietaria oficinalis*) and the cross-reactive allergen Parjl (from *Parietaria judaica*) and other atmospheric pollens including *Olea europaea*, *Artemisia* sp., gramineae, etc.

Tumor-associated Antigens

Tumor-associated antigens (or epitope-containing fragments thereof) include, but are not limited to, MAGE-2, MAGE-3, MUC-1, MUC-2, HER-2, high molecular weight melanoma-associated antigen MAA, GD2, carcinoembryonic antigen (CEA), TAG-72, ovarian-associated antigens OV-TL3 and MOV1 8, TUAN, alpha-feto protein (AFP), OFP, CA-125, CA-50, CA-19-9, renal tumor-associated antigen G250, EGP-40 (also known as EpCAM), S100 (malignant melanoma-associated antigen), p53, and p21ras. In some embodiments, a fragment of a TAA is used. A synthetic analog of any TAA (or epitope thereof), including any of the foregoing, may be used. Furthermore, combinations of one or more TAAs (or epitopes thereof) may be used.

Autoantigens

Autoantigens ("self antigens") that can be used include, but are not limited to, myelin basic protein or a fragment of myelin basic protein; proteolipid protein (PLP); HSP70; Ku (p70/p80) autoantigen, or its 80-kd subunit protein; the nuclear autoantigens La (SS-B) and Ro (SS-A); scleroderma antigens Rpp 30, Rpp 38 or Sc1-70; the centrosome autoantigen PCM-1; polymyositis-scleroderma autoantigen; scleroderma (and other systemic autoimmune disease) autoantigen CENP-A; U5, a small nuclear ribonucleoprotein (snRNP); the 100-kd protein of PM-Scl autoantigen; the nucleolar U3- and Th(7-2) ribonucleoproteins; the ribosomal protein L7; hPopl; and a 36-kd protein from nuclear matrix antigen; and the like. Suitable autoantigens also include Aβ protein (e.g., $A\beta_{1-42}$) associated with Alzheimer's Disease (see, e.g., Janus et al. (2003) *CNS Drugs* 17:457-474; and Nath et al. (2003) *Neuromolec. Med.* 3:29-39). Antigens also include altered self proteins such as prion proteins. Stolze et al. (2003) *Cell Mol Life Sci.* Mar;60(3): 629-38.

Microbial Pathogen-associated Antigens

Polypeptides and peptide epitopes associated with microbial pathogens are known in the art and include, but are not limited to, antigens associated with human immunodeficiency virus (HIV), e.g., HIV gp120, or an antigenic fragment thereof; cytomegalovirus antigens; *Mycobacterium* antigens (e.g., *Mycobacterium avium, Mycobacterium tuberculosis*, and the like); *Pneumocystic carinii* (PCP) antigens; malarial antigens, including, but not limited to, antigens associated with *Plasmodium falciparum* or any other malarial species, such as 41-3, AMA-1, CSP, PFEMP-1, GBP-130, MSP-1, PFS-16, SERP, etc.; fungal antigens; yeast antigens (e.g., an antigen of a *Candida* spp.); *toxoplasma* antigens, including, but not limited to, antigens associated with *Toxoplasma gondii, Toxoplasma encephalitis*, or any other *Toxoplasma* species; Epstein-Barr virus (EBV) antigens; and the like.

Pathogen-associated antigens are well known in the art; and many have been synthesized in the laboratory. See, e.g., U.S. Pat. No. 6,322,789, for a discussion of hepatitis B virus epitopes; U.S. Pat. No. 6,723,695 for a discussion of Epstein-Barr virus epitopes; etc.

Additional antigens of interest include antigens to which a person may have been exposed, including, but not limited to, *Mycobacterium bovis* (*Bacille Calmette-Guerin*); poxvirus antigens; and the like.

Further antigens of interest include antigens associated with or produced by weapons-grade pathogenic organisms ("biological warfare agents" or "bioterror agents"). Biological warfare agents include spore forming bacteria (e.g., anthrax), vegetative bacteria (e.g., plague, cholera), viruses (e.g., smallpox, yellow fever), and bacterial toxins (e.g., botulinum toxin, ricin).

Bacterial biological warfare agents include, but are not limited to, *Yersinia pestis, Bacillus anthracis, Vibro cholerae*, and the like. Bacterial biological warfare agents include bacteria that are developed, and/or produced, and/or used specifically for the purpose of inflicting disease and/or death upon a human population (where "human population" includes military personnel and civilian populations). Bacterial biological warfare agents include naturally-occurring (e.g., wild-type) bacteria as listed above; a naturally-occurring variant of any of the above-listed bacteria; and variants generated in the laboratory, including variants generated by selection, variants generated by chemical modification, and genetically modified variants (e.g., bacteria modified in a laboratory by recombinant DNA methods). Recombinant or synthetic viral biological warfare agents include variants of the above-listed bacteria that have increased virulence compared to a wild-type bacterium, and/or increased stability (e.g., storage stability at extreme high temperatures, and the like) compared to a wild-type bacterium, etc.

The term "viral biological warfare agent," as used herein, refers generally to any viral agent that is developed, and/or produced, and/or used specifically for the purpose of inflicting disease and/or death upon a human population (where "human population" includes military personnel and civilian populations). Such viral agents include, but are not limited to, Nipah virus; Hantavirus; alphaviruses that cause encephalitis, including, but not limited to, Venezuelan equine encephalitis virus, eastern equine encephalitis virus, and western equine encephalitis virus; and viruses that cause hemorrhagic fevers, including, but not limited to, filoviruses (e.g., Marburg virus, Ebola virus, and the like), Crimean Congo hemorrhagic fever virus, dengue virus, and arenaviruses (e.g., Lassa virus, Machupo virus, and the like). Also included in the term "viral biological warfare agents" are any subtype, serotype, isolate, or strain of any of the foregoing viruses.

The term "viral biological warfare agents" further includes naturally-occurring (e.g., wild-type) viruses as listed above; a naturally-occurring variant of any of the above-listed viruses; and variants generated in the laboratory, including variants generated by selection, variants generated by chemical modification, and genetically modified variants (e.g., virus modified in a laboratory by recombinant DNA methods). Variant viruses generated in the laboratory are referred to herein as "recombinant viruses" or "synthetic viruses." Recombinant or synthetic viral biological warfare agents include variants of the above-listed viruses that have increased virulence compared to a wild-type virus, and/or increased stability (e.g., storage stability at extreme high temperatures, and the like) compared to a wild-type virus, etc.

IL-15 Receptor Agonists

Any molecule that binds an IL-15 receptor and activates the receptor (e.g., acts as an IL-15 receptor agonist) can be used in the present methods. As such, an IL-15 receptor agonist includes, but is not limited to, naturally-occurring IL-15; recombinant IL-15, synthetic IL-15; modified IL-15; PEGylated IL-15; fusion proteins comprising IL-15 and a heterologous fusion partner; functional fragments of naturally-occurring IL-15 that bind to and activate an IL-15R; IL-15 mimetics; and the like. The IL-15 can produced in any convenient manner, including isolation of naturally-occurring IL-15 from human, mouse, rat, etc. tissues; production by synthetic means; production by recombinant means; and the like. IL-15 amino acid sequences are known in the art. See, e.g., GenBank Accession Nos. NP_751915, NP_751914, NP_000576, NP_037261, NP_032383, and P97604. IL-15 may comprise one or more modified amino acid residues, e.g., glycosylations, chemical modifications, and the like. The sequence of any known IL-15 polypeptide may be altered in various ways known in the art to generate targeted changes in sequence. A variant polypeptide will usually be substantially similar to the sequences provided herein, i.e. will differ by at least one amino acid, and may differ by at least two but not more than about ten amino acids. The sequence changes may be substitutions, insertions or deletions. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that may or may not alter the primary amino acid sequence include chemical derivatization of polypeptides, e.g., acetylation, or carboxylation; changes in amino acid sequence that introduce or remove a glycosylation site; changes in amino acid sequence that make the protein susceptible to modification with a polyethylene glycol moiety (PEGylation); and the like. Also included are modifications of glycosylation, e.g. those made by modifying the glycosylation patterns of a polypeptide during its synthesis and processing or in further processing steps; e.g. by exposing the polypeptide to enzymes that affect glycosylation, such as mammalian glycosylating or deglycosylating enzymes. Also embraced are sequences that have phosphorylated amino acid residues, e.g. phosphotyrosine, phosphoserine, or phosphothreonine.

An IL-15 polypeptide may comprise an N-blocked species, wherein the N-terminal amino acid is acylated with an acyl group, such as a formyl group, an acetyl group, a malonyl group, and the like. Also suitable for use is a consensus IL-15, e.g., an IL-15 that comprises an amino acid sequence that is a consensus of two or more known IL-15 amino acid sequences.

Also suitable for use are IL-15 polypeptides that have been modified using ordinary chemical techniques so as to improve their resistance to proteolytic degradation, to optimize solubility properties, or to render them more suitable as a therapeutic agent. For examples, the backbone of the peptide may be cyclized to enhance stability (see Friedler et al. (2000) *J. Biol. Chem.* 275:23783-23789). Analogs may be used that include residues other than naturally occurring L-amino acids, e.g. D-amino acids or non-naturally occurring synthetic amino acids. The protein may be pegylated to enhance stability. The polypeptides may be fused to albumin or another heterologous fusion partner.

An IL-15 polypeptide may be prepared by in vitro synthesis, using conventional methods as known in the art, by recombinant methods, or may be isolated from cells induced or naturally producing the protein. The particular sequence and the manner of preparation will be determined by convenience, economics, purity required, and the like. If desired, various groups may be introduced into the polypeptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

IL-15 polypeptides can be produced by any known method. DNA sequences encoding IL-15 may be synthesized using standard methods. In many embodiments, IL-15 polypeptides are the products of expression of manufactured DNA sequences transformed or transfected into bacterial hosts, e.g., *E. coli*, or in eukaryotic host cells (e.g., yeast; mammalian cells, such as CHO cells; and the like). In these embodiments, the IL-15 is "recombinant IL-15." Where the host cell is a bacterial host cell, the IL-15 may be modified to comprise an N-terminal methionine.

IL-7 Receptor Agonists

Any molecule that binds an IL-7 receptor and activates the receptor (e.g., acts as an IL-7 receptor agonist) can be used in the present methods. As such, an IL-7 receptor agonist includes, but is not limited to, naturally-occurring IL-7; recombinant IL-7; synthetic IL-7; modified IL-7; PEGylated IL-7; fusion proteins comprising IL-7 and a heterologous fusion partner; functional fragments of naturally-occurring IL-7 that bind to and activate an IL-7R; IL-7 mimetics; and the like. IL-7 amino acid sequences are known in the art. See, e.g., GenBank Accession Nos. P10168, NP_032397, NP_776349, AAH47698, and NP_037242. IL-7 may comprise one or more modified amino acid residues, e.g., glycosylations, chemical modifications, and the like. The sequence of any known IL-7 polypeptide may be altered in various ways known in the art to generate targeted changes in sequence. A variant polypeptide will usually be substantially similar to the sequences provided herein, i.e. will differ by at least one amino acid, and may differ by at least two but not more than about ten amino acids. The sequence changes may be substitutions, insertions or deletions. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that may or may not alter the primary amino acid sequence include chemical derivatization of polypeptides, e.g., acetylation, or carboxylation; changes in amino acid sequence that introduce or remove a glycosylation site; changes in amino acid sequence that make the protein susceptible to PEGylation; and the like. Also included are modifications of glycosylation, e.g. those made by modifying the glycosylation patterns of a polypeptide during its synthesis and processing or in further processing steps; e.g. by exposing the polypeptide to enzymes that affect glycosylation, such as mammalian glycosylating or deglycosylating enzymes. Also embraced are sequences that have phosphorylated amino acid residues, e.g. phosphotyrosine, phosphoserine, or phosphothreonine.

An IL-7 polypeptide may comprise an N-blocked species, wherein the N-terminal amino acid is acylated with an acyl group, such as a formyl group, an acetyl group, a malonyl group, and the like. Also suitable for use is a consensus IL-7, e.g., an IL-7 that comprises an amino acid sequence that is a consensus of two or more known IL-7 amino acid sequences.

Also suitable for use are IL-7 polypeptides that have been modified using ordinary chemical techniques so as to improve their resistance to proteolytic degradation, to optimize solubility properties, or to render them more suitable as a therapeutic agent. For examples, the backbone of the peptide may be cyclized to enhance stability (see Friedler et al. (2000) *J. Biol. Chem.* 275:23783-23789). Analogs may be used that include residues other than naturally occurring L-amino acids, e.g. D-amino acids or non-naturally occurring synthetic amino acids. The protein may be pegylated to enhance stability. The polypeptides may be fused to albumin or another heterologous fusion partner.

The polypeptides may be prepared by in vitro synthesis, using conventional methods as known in the art, by recombinant methods, or may be isolated from cells induced or naturally producing the protein. The particular sequence and the manner of preparation will be determined by convenience, economics, purity required, and the like. If desired, various groups may be introduced into the polypeptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

IL-7 polypeptides can be produced by any known method. DNA sequences encoding IL-15 may be synthesized using standard methods. In many embodiments, IL-7 polypeptides are the products of expression of manufactured DNA sequences transformed or transfected into bacterial hosts, e.g., *E. coli*, or in eukaryotic host cells (e.g., yeast; mammalian cells, such as CHO cells; and the like). In these embodiments, the IL-7 is "recombinant IL-7." Where the host cell is a bacterial host cell, the IL-7 may be modified to comprise an N-terminal methionine.

Utility

The instant methods of detecting antigen-specific T lymphocytes are useful in a wide variety of diagnostic assays, clinical studies, and monitoring assays.

In some embodiments, a subject method is useful for determining the extent of an infection or the extent of a disease such as infection with a pathogenic organism, cancer, allergy, an autoimmune disorder, etc. Thus, e.g., the instant methods are useful for detecting T lymphocytes that are specific for antigens associated with a pathogen; T lymphocytes that are specific for a tumor-associated antigen; T lymphocytes that are specific for an allergen; and T lymphocytes that are specific for a self antigen. The methods are thus useful for staging a disorder.

In some embodiments, a subject method is useful for identifying to which allergen(s) an individual is sensitive, e.g., to which allergen(s) an individual exhibits an allergic reaction. Thus, e.g. T lymphocytes in a biological sample from an individual are exposed to a panel of allergens, so that the allergen(s) to which T lymphocytes in the sample are reactive can be identified.

The subject methods are useful for monitoring the progression of a disease or disorder over time. Thus, for example, samples are taken from an individual at certain intervals over a period of time, where a change in the level of antigen-specific T lymphocytes over time is an indication of the progression of the disease or disorder.

In other embodiments, the methods are useful for determining the efficacy of a treatment for a disorder. In some embodiments, the present invention provides methods of determining the response of an individual to treatment for an infection with a pathogen. In other embodiments, the present invention provides methods of determining the response of an individual to treatment for cancer. In other embodiments, the present invention provides methods of determining the response of an individual to treatment for allergy.

In other embodiments, the methods are useful for determining the exposure of an individual to a biological warfare agent.

In other embodiments, the methods are useful for clinical studies, e.g., to compare the level of antigen-specific T lymphocytes from one individual to another, e.g., in response to treatment, in the absence of treatment, etc.

In other embodiments, a subject method is useful for testing efficacy of a vaccine. For example, the level of T lymphocytes specific for an antigen in a vaccine preparation, in a biological sample from an individual who has received the vaccine is compared to the level of T lymphocytes specific for the same antigen in a biological sample from an individual who has received a placebo.

In some embodiments, a subject method provides for detecting T lymphocytes that are specific for antigens associated with a pathogen; T lymphocytes that are specific for a tumor-associated antigen; T lymphocytes that are specific for an allergen; or T lymphocytes that are specific for a self antigen. In these embodiments, a cell sample is combined with an appropriate antigen, an IL-15R agonist, and an IL-7R agonist to form a test sample. T lymphocytes specific for the antigen is detected as described above.

Based on the results of the assay for the detection of antigen-specific T lymphocytes, an appropriate treatment regimen can be determined, or a current treatment regimen can be altered as appropriate.

The following provides non-limiting examples of utilities of a subject method.

Assays for T Lymphocytes Specific for a Pathogen-associated Antigen

In some embodiments, a subject method provides for detection of an antigen-specific T lymphocyte in an individual, where the antigen is a pathogen-associated antigen. The assay generally involves contacting a biological sample from an individual being tested with an IL-15R agonist, an IL-7R agonist, and a pathogen-associated antigen, forming a test sample; and detecting in the test sample a level of T lymphocyte specific for the pathogen-associated antigen. A suitable negative control is a sample that includes a biological sample from the same individual, an IL-15R agonist, an IL-7R agonist, and a protein unrelated to the pathogen-associated antigen (e.g., albumin, glucose-6-phosphate dehydrogenase, and the like). A suitable positive control is a sample that includes a biological sample containing T lymphocytes that are specific for a pathogen-associated antigen, an IL-15R agonist, and an IL-7R agonist. Typically the same pathogen-associated antigen that is used in the test sample is used in the positive control sample. The positive control sample will typically employ T lymphocytes that are specific for the pathogen-associated antigen, e.g., an established T cell line, T lymphocytes from an individual known to be infected with a pathogen that produces the pathogen-associated antigen, and the like.

In some embodiments, a subject method will further include a step to determine whether an antigen-specific T cell detected by a subject method is an effector T cell or a memory T cell. Such a step provides information for staging of the disease. Such a step also permits discrimination between an active pathogen infection and exposure to a pathogen (without active infection). If an active infection is present, antigen-specific T cells would be expected to be activated T cells. If the individual has been exposed to a pathogen, but does not have an active infection, antigen-specific T cells would be expected to be memory T cells.

As one non-limiting example, a subject method provides for detection of an antigen-specific T lymphocyte in an individual, where the antigen-specific T lymphocyte is specific for a human immunodeficiency virus (HIV) antigen. A cell sample is taken from an individual being tested for the presence of T lymphocytes specific for an HIV antigen. Such individuals include, but are not limited to, individuals who have been diagnosed as having an HIV infection; individuals at risk for HIV infection due to sexual activity with HIV-infected individuals; intravenous drug users; individuals who may have been exposed to HIV-infected blood, blood products, or other HIV-contaminated body fluids; babies who are being nursed by HIV-infected mothers. In some of these embodiments, the individual is CD4$^+$ T cell deficient. In other embodiments, the individual has not yet been diagnosed as having an HIV infection. In some of these embodiments, the individual is asymptomatic.

A biological sample from the individual is tested for the presence of T lymphocytes specific for an HIV antigen. Based on the results of the test, a diagnosis of HIV infection may be made. Where the individual has previously been diagnosed as HIV positive, a subject method is useful for assisting in determining the appropriate treatment.

In some embodiments, a subject method is useful for determining the efficacy of a given treatment for HIV infection. Thus, e.g., at various intervals during a course of treatment for HIV infection, a biological sample is taken from an individual and the level of T lymphocytes specific for an HIV antigen is determined. In some embodiments, an increase or decrease in the level of T lymphocytes specific for an HIV antigen is an indication that the course of treatment has been effective in reducing the level of HIV in the peripheral blood, or eliminating HIV from the peripheral blood; and increasing the number of $CD4^+$ T cells in the peripheral blood, or restoring $CD4^+$ T cell levels to within a normal range.

Assays for Mycobacterial Infection

In some embodiments, a subject method provides for detection of an antigen-specific T lymphocyte in an individual, where the antigen-specific T lymphocyte is specific for a mycobacterial antigen. Mycobacterial antigens include antigens associated with any mycobacterial species, including, but not limited to, *Mycobacterium tuberculosis, M. avium* (also known as the *mycobacterium avium* complex or *M. avium-intracellulare*), *M. bovis* (*Bacille Calmette-Guerin*), *M. leprae, M. kansasii, M. fortuitum, M. chelonae,* and *M. abscessus.*

Assays for T lymphocytes specific for *M. tuberculosis* are useful for determining whether an individual has mounted an immune response against *M. tuberculosis*. In these embodiments, a biological sample from the individual is combined with an *M. tuberculosis* antigen, an IL-15R agonist, and an IL-7R agonist, to form a test sample; and the level of T lymphocytes in the test sample that are specific for an *M. tuberculosis* antigen is detected.

In some embodiments, a subject method provides for determining the efficacy of a treatment for a mycobacterial infection. A given treatment is considered efficacious if the level of T lymphocytes specific for an *M. tuberculosis* antigen decreases during or after a course of treatment for an *M. tuberculosis* infection.

Assay for Exposure to a Biological Warfare Agent

In some embodiments, a subject method provides for detection of an antigen-specific T lymphocyte, in an individual, where the antigen-specific T lymphocyte is specific for a biological warfare agent. The presence in the individual of a T lymphocyte specific for an epitope on an antigen associated with or produced by a biological warfare agent indicates that the individual has been exposed to the agent. An individual may be tested following a known or suspected exposure.

Assay to Identify the Allergen(s) to which an Individual is Sensitive

In some embodiments, a subject method is useful for identifying to which allergen(s) an individual is sensitive, e.g., to which allergen(s) an individual exhibits an allergic reaction. Thus, e.g. T lymphocytes in a biological sample from an individual are exposed to a panel of allergens, so that the allergen(s) to which T lymphocytes in the sample are reactive can be identified.

In these embodiments, a biological sample from the individual is combined with an allergen, an IL-15R agonist, and an IL-7R agonist, to form a test sample; and the level of T lymphocytes specific for the allergen is detected. In many embodiments, a panel of allergens is tested. Thus, a plurality of test samples is formed, each of which contains, in addition to the biological sample, an allergen, an IL-15R agonist, and an IL-7R agonist. After a suitable period of time, allergen-specific T lymphocytes in the individual sample are detected. Suitable negative controls include a sample comprising a biological sample from the same individual, an IL-15R agonist, an IL-7R agonist, and a protein to which the individual is not allergic (e.g., albumin, G6PDH, and the like). A suitable positive control is a sample that includes a biological sample from an individual known to be allergic to ragweed antigen, a ragweed antigen, an IL-15R agonist, and an IL-7R agonist. Another suitable positive control is a sample that includes T lymphocytes (e.g., an established T cell line) that are known to be specific for a given allergen, an IL-15R agonist, and an IL-7R agonist.

Assay for the Presence of Self-reactive T Lymphocytes

In some embodiments, a subject method is useful for detecting autoreactive (self-reactive) T lymphocytes in a biological sample. In these embodiments, the methods generally involve contacting a biological sample, from an individual, with an IL-15R agonist, an IL-7R agonist, and an autoantigen; and detecting the level of T lymphocytes in the test sample that are specific for the autoantigen. A suitable negative control is a sample that includes an IL-15R agonist, an IL-7R agonist, an antigen that is not a self antigen (e.g., a bacterial antigen, a viral antigen, or other antigen that is not cross-reactive with the self antigen that is included in the test sample), and a biological sample from the same individual as the biological sample being tested. A suitable positive control is a sample that includes an IL-15R agonist, an IL-7R agonist, the same self antigen as in the test sample, and T lymphocytes that are specific to the self antigen (e.g., an established T cell line, T lymphocytes from an individual having T lymphocytes specific for the autoantigen found in the test sample, etc.

In some embodiments, e.g., where the autoantigen(s) to which the individual may be reacting is(are) unknown, the assay will employ a panel of possible autoantigens. In other embodiments, e.g., where other symptoms are present that point toward a particular autoimmune disorder, an autoantigen(s) that is relevant to the particular autoimmune disorder is used. Similarly, where the individual has been diagnosed with an autoimmune disorder, and the assay is used to determine whether a given treatment for the autoimmune disorder, an autoantigen(s) that is relevant to the particular autoimmune disorder is used.

Assays to Test the Efficacy of an Immunogenic Composition

In some embodiments, a subject method is useful to test the efficacy of an immunogenic composition such as an experimental vaccine. In these embodiments, the methods generally involve a) contacting a first biological sample, from a test individual to whom a vaccine composition comprising an antigen has been administered, with an IL-15R agonist, an IL-7R agonist, and the antigen present in the vaccine composition, forming a test sample; contacting a second biological sample, from a control individual to whom the vaccine composition was not administered, with an IL-15R agonist, an IL-7R agonist, and the antigen present in the vaccine composition, forming a control (placebo) sample; and detecting in the test sample and the control sample the level of T lymphocytes that are specific for the antigen. Where the level of T lymphocytes specific for the antigen in the vaccine composition is at least about 2-fold, at least about 5-fold, at least about 10-fold, at least about 15-fold, at least about 25-fold, or at least about 50-fold, or more, higher in the test sample than in the control sample, the vaccine is considered to be efficacious in eliciting an antigen-specific immune response.

Kits and Systems

The present invention provide kits and systems for use in carrying out a subject method. In some embodiments, a subject kit includes: a) an antibody or other capture reagent that is specific for a secreted factor produced by an antigen-specific T lymphocyte, where the capture reagent (e.g., an antibody) is immobilized on an insoluble support; b) an IL-15R agonist; and c) an IL-7R agonist. The components of the kit are provided in a suitable storage medium/media. In some embodiments, one or more antigens is also provided. Generally, the capture reagent, the antigen, the IL-15R agonist, and the IL-7R agonist are provided in separate vials, although in some embodiments, two or more of these components may be combined in a single vial. A subject kit may further include one or more reagents such as a buffer, reagents for developing an enzyme-linked assay (e.g., a substrate), and the like. A subject system includes a subject kit, and instrumentation for use in the detection step of a subject method.

In some embodiments, a subject kit further includes one or more antigens, e.g., one or more antigens associated with a given pathogen or pathogens; one or more M. tuberculosis antigens; one or more allergens; one or more tumor-associated antigens; one or more autoantigens; or one or more antigens associated with or produced by a biological warfare agent. In some embodiments, a subject kit includes a panel of For example, in some embodiments, a subject kit may further include a panel of allergens; a panel of antigens associated with various pathogens; a panel of HIV antigens; a panel of tumor-associated antigens; and the like.

A subject kit will in many embodiments include components for a positive and/or a negative control. For example, in some embodiments, a subject kit will include, for use in a positive control, T lymphocytes that are specific for the same antigen(s) that are included in the test sample. A positive control could also include a biological sample containing T lymphocytes stimulated with staphylococcal enterotoxin B (SEB). Thus, in some embodiments, a subject kit will further include SEB. In some embodiments, a subject kit will include, for use in a negative control, an antigen (a "negative control antigen") that is unrelated to (e.g., immunologically not cross-reactive, also referred to as an "irrelevant antigen") the antigen included in the test sample. A negative control antigen is an antigen that is not recognized and bound by a TCR on the surface of a T lymphocyte that is specific for a test antigen, e.g., a negative control antigen is immunologically not cross-reactive with the test antigen.

In some embodiments, a subject kit will include one or more antibodies that bind a Class I MHC polypeptide, for reducing detection of CD8$^+$ T cells in the sample. In other embodiments, a subject kit will include one or more antibodies that bind a Class II MHC polypeptide, for reducing detection of CD4$^+$ T cells in the sample.

In some embodiments, a subject kit will include one or more antibodies that bind a CD4 polypeptide, for reducing detection of CD4$^+$ T cells in the sample. In some embodiments, the antibody will be attached to an insoluble support (e.g., a magnetic bead or other insoluble support), for removing CD4$^+$ T cells from the sample. In some embodiments, the antibody will be one that binds complement, and the kit will further include complement. Antibodies specific for CD4 polypeptides are commercially available; and any known antibody specific for CD4 can be used.

In other embodiments, a subject kit will include one or more antibodies that bind a CD8 polypeptide, for reducing detection of CD8$^+$ T cells in the sample. In some embodiments, the antibody will be attached to an insoluble support (e.g., a magnetic bead or other insoluble support), for removing CD8$^+$ T cells from the sample. In some embodiments, the antibody will be one that binds complement, and the kit will further include complement. Antibodies specific for CD8 polypeptides are commercially available; and any known antibody specific for CD9 can be used.

In some embodiments, a subject kit will include one or more antibodies that permit discrimination between effector T cells and memory T cells. CD27 is a marker of T cell activation. Antibody to CD27 will in some embodiments be included in a subject kit, to allow detection of activated T cells. CD45RA/CD45RO is a marker of memory T cells. Antibody to CD45RA/CD45RO will in some embodiments be included in a subject kit, to allow detection of memory T cells. Other methods of discriminating between effector T cells and memory T cells include detecting a level of CCR7 and/or a level of CD62L. High expression of CCR7 and CD62L is indicative of a memory T cell; low expression of CCR7 and CD62L is indicative of an effector T cell. See, e.g., Wherry and Ahmed (2004) J. Virol. 78:5535-5545. Thus, in some embodiments, a subject kit will include an antibody specific for CCR7. In some embodiments, a subject kit will include an antibody specific for CD62L.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., computer diskette, or compact disc, or memory key, etc., on which the information has been recorded. Yet another means would be a digital versatile disk, video tape, etc. Yet another means that may be present is a website address which may be used via the internet to access the information at a removed site. Any convenient means may be present in a subject kit.

In some embodiments, a system is provided, which includes a subject kit, and instrumentation for detection. For example, where the assay is a colorimetric assay, a subject system includes a subject kit; and a spectrophotometer; where the assay provides for a luminescent signal, a subject system includes a subject kit; and a luminometer; where the assay method is ELISPOT, the instrumentation for detection is an ELISPOT reader; etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s, second(s); min, minute(s); hr, hour(s); SEM, standard error of the mean; and the like.

Example 1

Detection of Antigen-specific T Lymphocytes

Methods

Peripheral Blood Mononuclear Cells and Donors

Heparinized blood samples were obtained, with informed consent, from healthy donors among some were known to be vaccinated with the *Bacillus Calmette-Guerin* (BCG) vaccine (a live vaccine prepared from an attenuated strain of *Mycobacterium bovis*), or had a known cellular response against cytomegalovirus (CMV). PBMC were isolated by density gradient centrifugation using Ficoll-Hypaque (Pharmacia, Uppsala, Sweden). Cells were either used fresh or were kept frozen at −140° C. (vapor phase of liquid nitrogen) in fetal calf serum (FCS) (Gemini Bioproducts, Woodland, Calif., USA) containing 10% dimethyl sulfoxide (Sigma-Aldrich, St. Louis, Mo., USA).

Protein and Peptide Preparations

IFN-γ production by CD4+ or CD8+ T cells was assessed in response to stimulation with protein antigen or synthetic peptides, respectively. Purified protein derivative (PPD) (Staten Serum Institute, Copenhagen, Denmark) was used as protein antigen. Synthetic peptides included HLA-A*0201-restricted immunodominant epitopes from cytomegalovirus (CMV) matrix protein pp65, (495-503, NLVPMVATV; SEQ ID NO:01) and human immunodeficiency virus type-1 (HIV-1) Gag (77-85, SLYNTVATL; SEQ ID NO:02), and an HLA-B*35-restricted epitope from HIV-1 Pol (329-337, HPDIVIYQY; SEQ ID NO:03). As a negative control, peripheral blood mononuclear cells (PBMC) were stimulated with media alone. As a positive control, PBMC were stimulated with staphylococcal enterotoxin B (SEB) (Sigma-Aldrich, St. Louis, Mo., USA).

ELISPOT Assay

For ELISPOT assays, 96-well nitrocellulose-bottom plates (Multiscreen-HA, Millipore, Molsheim, France) were coated with 50 µl/well of anti-human IFN-γ at a concentration of 5 µg/ml (1-D1K, Mabtech, Nacka, Sweden) and incubated at 4° C. overnight. The following day, plates were washed four times in phosphate-buffered saline (PBS) and blocked with 50 µl/well of culture medium (RPMI containing 15% FCS, 1% L-glutamine, 1% penicillin-streptomycin and HEPES buffer). Cytokine cocktails were prepared containing IL-7 and IL-15 (R&D Systems, Minneapolis, Minn., USA) in concentrations ranging from 1 to 100 ng/ml. For some experiments, co-stimulatory antibodies anti-CD28 and anti-CD49d were added at 1 µg/ml (Becton Dickinson, San Jose, Calif., USA). 100 µl of medium, with or without cytokines and co-stimulatory antibodies, was distributed to replicate wells of the ELISPOT plate. Antigens were added such that final concentrations were 10 µg/ml for PPD and 10 µg/ml for synthetic peptides. PBMC ($2\times10^5$) were then added in a volume of 50 µl, bringing the total volume in each well to 200 µl. Incubation was continued overnight (16-18 hours) at 37° C., 5% $CO_2$.

ELISPOT plates were developed as previously described (Larsson et al., 1999, supra). Briefly, plates were washed four times with PBS containing 0.05% Tween-20 (Sigma-Aldrich, St-Louis, Mo., USA) and incubated for two hours with 50 µl/well of biotinylated anti-human IFN-γ at a concentration of 1 µg/ml (7-B6-1, Mabtech, Nacka, Sweden) at 37° C. Plates were then washed four times in PBS with 0.1% Tween-20 and incubated for one hour with avidin-bound biotinylated horseradish peroxidase (Vector Laboratories, Burlingame, Calif., USA) at room temperature. ELISPOT plates were washed again four times in PBS with 0.1% Tween-20 and developed by incubating for 5 minutes with stable diaminobenzidine substrate (DAB, Research Genetics, Huntsville, Ala., USA), followed by rinsing in tap water. Spots were counted with the aid of an ELISPOT-Series 4 Analyser (Cell Technology Inc., Jessup, Md., USA), totals for duplicate or triplicate wells were averaged and normalised to numbers of IFN-γ spotforming cells per $1\times10^6$ PBMC. Average values for negative medium control wells were subtracted from the average values from antigen-stimulated wells.

Results

Enhanced ELISPOT Detection of CD4+ T Cell Responses in Fresh and Cryopreserved PBMC by Addition of Both IL-7 and IL-15

Frequencies of CD4+ T cells reactive against PPD were analyzed by ELISPOT in fresh and cryopreserved PBMC from two donors (donors 1 and 2) known to be vaccinated with BCG. The results are shown in FIGS. 1A and 1B.

Figure 1B:
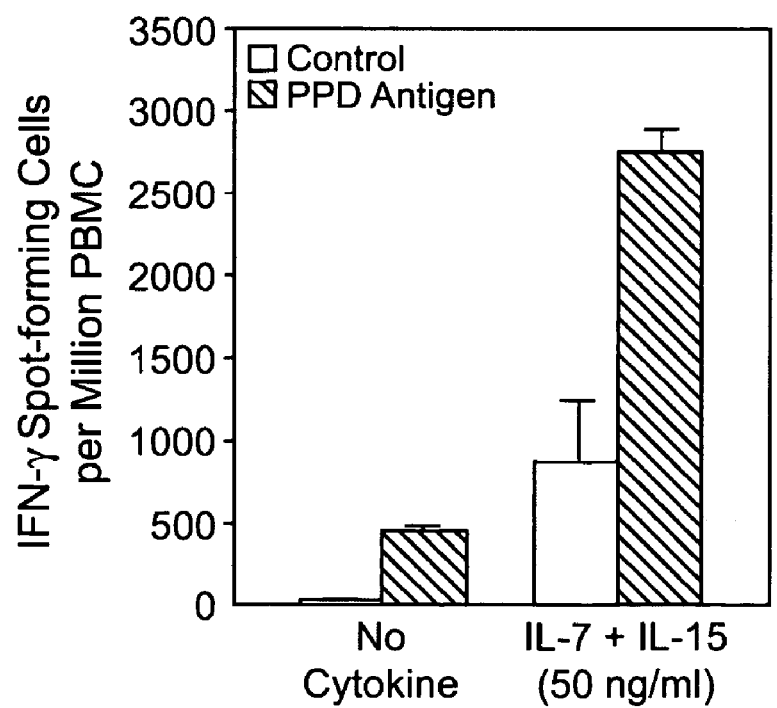

FIGS. 1A and 1B: ELISPOT detection of PPD-specific CD4+ T cell responses in fresh (FIG. 1A) and cryopreserved (FIG. 1B) PBMC from donor 1 with addition of both IL-7 and IL-15. ELISPOT wells containing $2\times10^5$ PBMC were stimulated with medium alone; 10 µg/ml of PPD; medium supplemented with 50 ng/ml of IL-7 and IL-15; or 10 µg/ml of PPD supplemented with 50 ng/ml of IL-7 and IL-15. FIG. 1A (fresh PBMC) shows averaged values from duplicate wells normalized to numbers of IFN-γ spot-forming cells per $1\times10^6$ PBMC for the different stimulation conditions, error bars represent the standard error of the mean. FIG. 1B (cryopreserved PBMC) shows averaged values from duplicate wells normalized to numbers of IFN-γ spot-forming cells per $1\times10^6$ PBMC for the different stimulation conditions, error bars represent the standard error of the mean.

PBMC were incubated overnight in duplicate wells in the presence of media alone, PPD, media supplemented with 50 ng/ml of both IL-7 and IL-15, and PPD supplemented with 50 ng/ml of both IL-7 and IL-15 (FIG. 1A, fresh PBMC from donor 1; FIG. 1B, cryopreserved PBMC from donor 1).

For fresh PBMC, addition of both IL-7 and IL-15 to the PPD-stimulation resulted in an increase in the number of PPD-specific IFN-γ secreting cells per million PBMC by a factor of 1.6 for donor 1 (mean±SEM: 2635±77.5 vs. 1670±155.0, FIG. 1A) and by a factor of 2.4 for donor 2 (605±122.5 vs. 250±25.0). Addition of IL-7 and IL-15 enhanced spontaneous IFN-γ release in medium control wells by a factor of 9.7 (145±60.0 vs. 15±7.5, FIG. 1A) for donor 1 and by a factor of 19 (95±40.0 vs. 5±5.0) for donor 2.

In the absence of IL-7 and IL-15, the number of PPD-specific IFN-γ secreting cells was significantly lower in cryopreserved PBMC compared to fresh PBMC (420±27.5 vs. 1670±155.0 for donor 1, factor 0.25, FIG. 1A and FIG. 1B; 55±25.0 vs. 250±25.0 for donor 2, factor 0.22). Addition of IL-7 and IL-15 to PPD in cryopreserved PBMC augmented the number of PPD-specific IFN-γ secreting cells by a factor of 4.7 for donor 1 (1970±150.0 vs. 420±27.5, FIG. 1B) and by a factor of 18 for donor 2 (980±242.5 vs.

55±25.0), restoring these responses to levels near those observed in fresh PBMC. The combination of IL-7 and IL-15 also enhanced spontaneous IFN-γ release by cryopreserved PBMC in medium control wells, by a factor of 77 (765±362.5 vs. 10±2.5, FIG. 1B) for donor 1 and by a factor of 38 (190±72.5 vs. 5±5.0) for donor 2.

For both donors, PPD-specific IFN-γ-producing lymphocytes were CD4+ T cells as demonstrated by intracellular cytokine flow cytometry using monoclonal antibodies specific for IFN-γ, CD4 and CD8.

Enhanced ELISPOT Detection of CD8+ T Cell Responses in Fresh PBMC by Addition of IL-7 and IL-15

Frequencies of CD8+ T cells reactive against the HLA-A*0201-restricted immunodominant epitope from CMV matrix protein pp65 (NLVPMVATV; SEQ ID NO:01) were analyzed by ELISPOT in freshly isolated PBMC from an HLA-A*02-positive donor (donor 3). The results are shown in FIG. 2.

Figure 2:
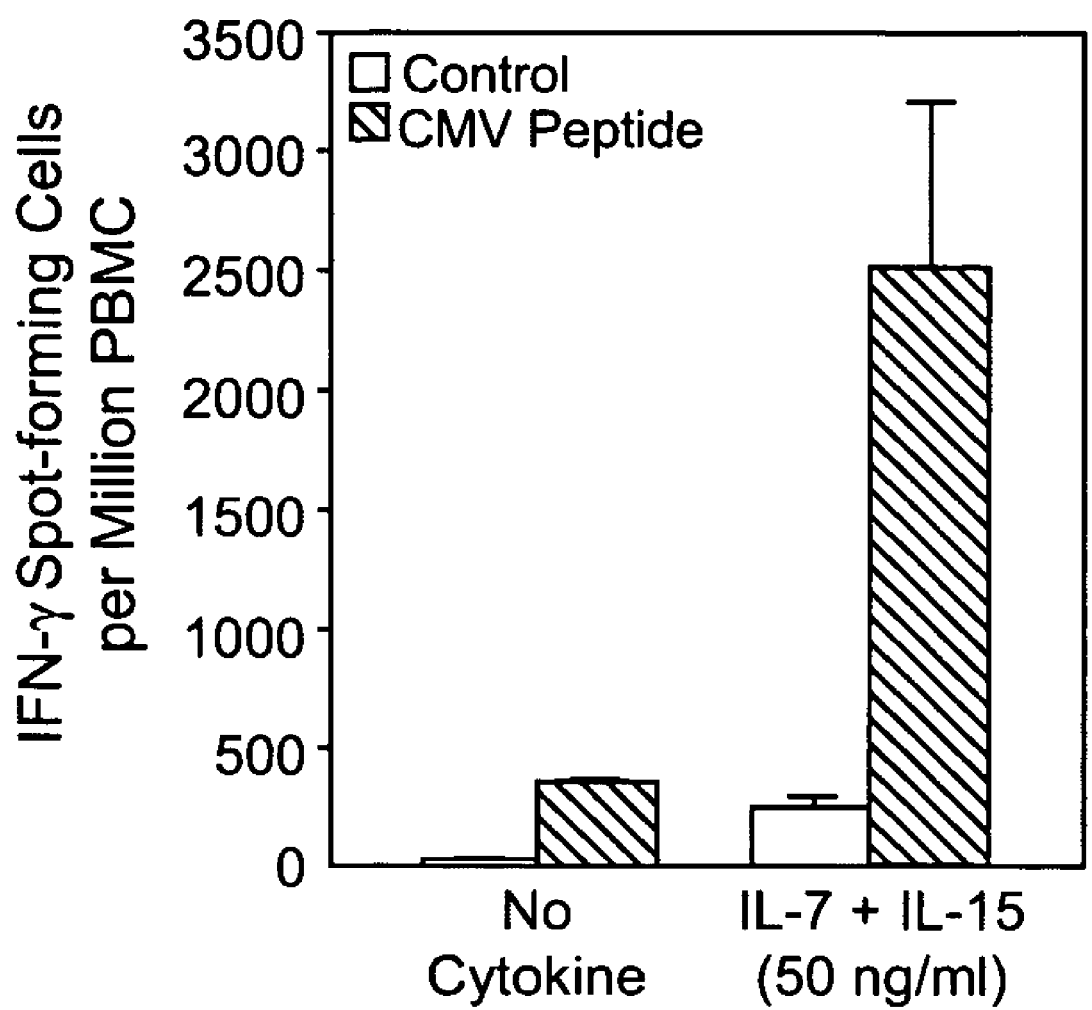
FIG. 2 depicts ELISPOT detection of CD8+ T cell responses specific for an immunodominant HLA-A*0201-restricted epitope from CMV matrix protein pp65 in fresh PBMC from donor 3 with addition of both IL-7 and IL-15.

FIG. 2: ELISPOT detection of CD8+ T cell responses specific for an immunodominant HLA-A*0201-restricted epitope from CMV matrix protein pp65 in fresh PBMC from donor 3 with addition of both IL-7 and IL-15. ELISPOT wells contained $2 \times 10^5$ PBMC stimulated with medium alone; 10 μg/ml CMV peptide; medium supplemented with 50 ng/ml of IL-7 and IL-15; or 10 μg/ml of CMV peptide supplemented with 50 ng/ml of IL-7 and IL-15. Bars represent averaged values from triplicate wells normalised to numbers of IFN-γ spot-forming cells per $1 \times 10^6$ PBMC for the different stimulation conditions, error bars represent the standard error of the mean.

PBMC were incubated overnight in triplicate wells in the presence of media alone, CMV peptide, media supplemented with 50 ng/ml of IL-7 and/or IL-15, and CMV peptide supplemented with 50 ng/ml of IL-7 and/or IL-15 (FIG. 2).

Addition of both IL-7 and IL-15 to CMV peptide resulted in a 7.5-fold increase in the number of IFN-γ secreting cells per million PBMC as compared to CMV peptide alone (mean±SEM: 2285±675.5 vs. 305±1.7, FIG. 2). Addition of both IL-7 and IL-15 enhanced the spontaneous release of IFN-γ in medium control wells by a factor of 10 (200±58.5 vs. 20±1.7, FIG. 2).

As opposed to the combined addition of the cytokines, the individual addition of IL-15 to CMV peptide only resulted in a marginal increase in the number of IFN-γ secreting cells compared to CMV peptide alone (mean±SEM: 370±117.6 vs. 305±2.9, factor 1.2), while the addition of IL-7 individually did not have any effect at all (300±70.1 vs. 305±2.9, factor 0.98).

Figure 3A:
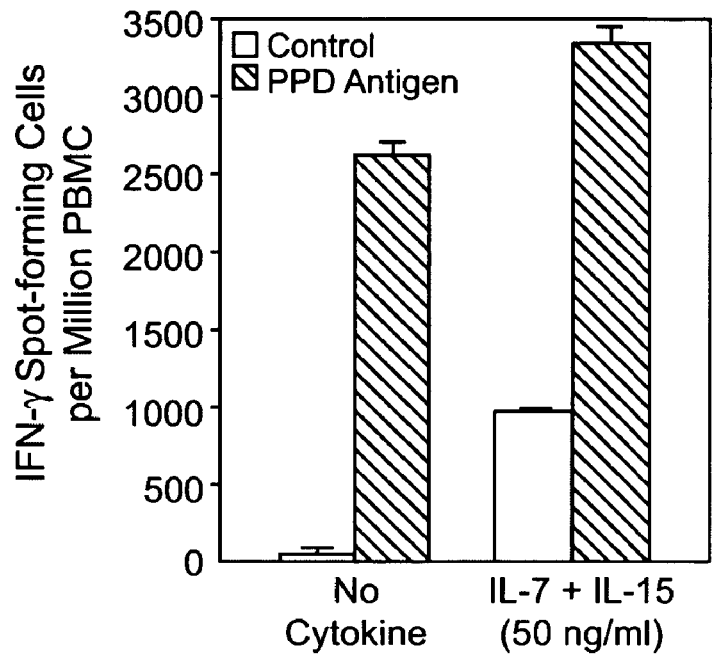
FIGS. 3A and 3B depict combination of IL-7 and IL-15 with antibody to co-stimulatory molecule CD28 (α-CD28) and antibody to co-stimulatory molecule CD49d (α-CD49d) in ELISPOT detection of PPD-specific CD4+ T cell responses in fresh (3A) and cryopreserved (3B) PBMC from donor 1.
Figure 3B:
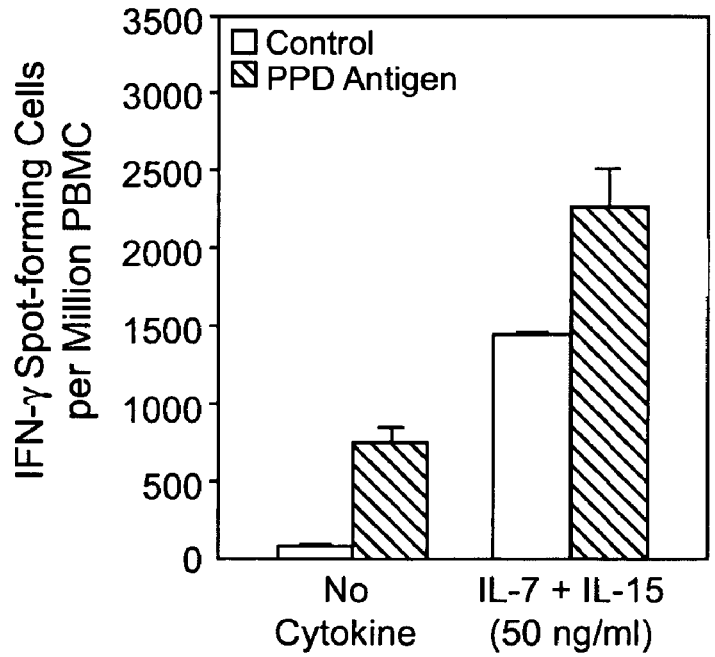

Combination of Both IL-7 and IL-15 with Co-stimulatory Antibodies Provides No Additional Enhancement Addition of co-stimulatory antibodies anti-CD28 and anti-CD49d to PPD stimulation, in the absence of cytokines, resulted in increased numbers of PPD-specific IFN-γ secreting cells compared to PPD stimulation alone, by a factor of 1.5 for fresh PBMC from donor 1 (mean±SEM: 2550±70 vs. 1670±155, FIG. 3A and FIG. 1A) and by a factor of 1.5 for cryopreserved PBMC from donor 1 (625±120 vs. 420±27.5, FIG. 3B). For fresh PBMC from donor 1, the enhancement of PPD-specific IFN-γ secretion provided by co-stimulatory antibodies equalled that induced by IL-7 and IL-15 (factor 1.5 vs. 1.6), but was much lower for cryopreserved PBMC from donor 1 (factor 1.5 vs. 4.7). The same conclusions were valid for donor 2.

When both cytokines (IL-7 and IL-15) and co-stimulatory antibodies (anti-CD28 and anti-CD49d) were combined with PPD stimulation of PBMC from donor 1, no significant additive effects were observed. Although the total number of IFN-γ secreting cells was increased compared to stimulation with PPD alone (2470±107.5 vs. 1670±155 for fresh PBMC, factor 1.5, FIG. 3A and FIG. 1A; 805±270 vs. 420±27.5 for cryopreserved PBMC, factor 1.9, FIG. 3B and FIG. 1B), the magnitude of the increase was comparable to or lower than that observed when cytokines or co-stimulatory antibodies were added individually to PPD. This effect was explained by a sharp increase in background release of IFN-γ in wells treated with both cytokines and co-stimulatory antibodies, as shown in medium control wells (935±10 vs. 15±7.5 for fresh PBMC, factor 62, FIG. 3A and FIG. 1A; 1340±2.5 vs. 10±2.5 for cryopreserved PBMC, factor 134, FIG. 3B and FIG. 1B). The same conclusions were valid for donor 2.

FIGS. 3A and 3B: Combination of IL-7 and IL-15 with antibodies to co-stimulatory molecules CD28 and CD49d in ELISPOT detection of PPD-specific CD4+ T cell responses in fresh (FIG. 3A) and cryopreserved (FIG. 3B) PBMC from donor 1. Bars represent averaged values from duplicate wells normalized to numbers of IFN-γ spot-forming cells per $1 \times 10^6$ PBMC for the different stimulation conditions, error bars represent the standard error of the mean. Concentration of anti-CD28 and anti-CD49d antibodies was 1 μg/ml.

Optimal Cytokine Concentrations

The cytokines IL-7 and IL-15 were added to PPD in the ELISPOT assay using cryopreserved PBMC from donors 1 and 2, in concentrations ranging from 1 ng/ml to 100 ng/ml for both cytokines. The results are shown in FIG. 4.

Figure 4:
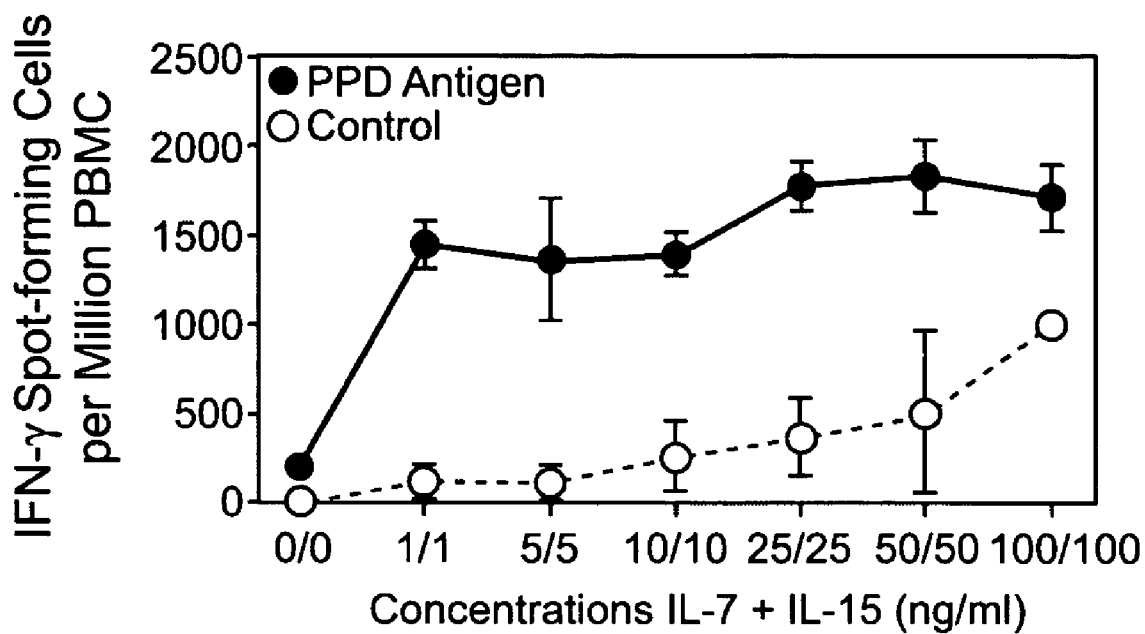
FIG. 4 depicts titration of cytokine concentrations. Cytokines IL-7 and IL-15 at concentrations ranging from 1 ng/ml to 100 ng/ml were applied to ELISPOT detection of PPD-specific CD4+ T cell responses in cryopreserved PBMC from donor 1.

FIG. 4: Titration of cytokine concentrations. Cytokines IL-7 and IL-15 at concentrations ranging from 1 ng/ml to 100 ng/ml were applied to ELISPOT detection of PPD-specific CD4+ T cell responses in cryopreserved PBMC from donor 1. Averaged values from duplicate wells normalized to numbers of IFN-γ spot-forming cells per $1 \times 10^6$ PBMC are shown, error bars represent the standard error of the mean.

For donor 1, addition of IL-7 and IL-15 at a concentration as low as 1 ng/ml resulted in a 7.3-fold increase. in the number of PPD-specific IFN-γ secreting cells compared to PPD alone (mean±SEM: 1315±107.6 vs. 180±10, FIG. 4). The magnitude of enhancement was not significantly increased when higher concentrations of cytokines were added. The maximal enhancement observed was 7.9-fold, at IL-7 and IL-15 concentrations of 50 ng/ml (FIG. 4). However, augmenting the concentrations of IL-7 and IL-15 in medium control wells also resulted in increased spontaneous release of IFN-γ, thereby reducing the net enhancement of PPD-specific responses. Concentrations in the 1-5 ng/ml range appeared to provide maximal enhancement of antigen-specific responses with minimal increases in background spontaneous IFN-γ release. The same results were obtained for donor 2.

Induction of Primary Responses Against HIV-1 Peptides by Addition of Both IL-7 and IL-15

Frequencies of CD8+ T cells reactive against an HLA-A*0201-restricted human immunodeficiency virus type-1 (HIV-1) Gag peptide epitope (77-85, SLYNTVATL; SEQ ID NO:2) and an HLA-B*35-restricted HIV-1 Pol peptide epitope (329-337, HPDIVIYQY; SEQ ID NO:03), were analyzed by ELISPOT in cryopreserved PBMC from two donors (donors 3 and 4) without known exposure to HIV. Both donors were HLA-A*02-positive, donor 3 was HLA-B*35-negative and donor 4 was HLA-B*35 positive. PBMC were incubated overnight in duplicate wells in the presence of media alone, HIV-1 peptides, media supplemented with 50 ng/ml of both IL-7 and IL-15, and HIV-1 peptides supplemented with 50 ng/ml of both IL-7 and IL-15.

In the absence of IL-7 and IL-15, neither donor mounted a response against the Gag peptide or the Pol peptide (mean±SEM: 15±2.5 and 15±2.5 respectively for donor 3; 25±15 and 15±5 respectively for donor 4). In the presence of IL-7 and IL-15, however, a significant increase was observed in the response of donor 3 against the Gag peptide (120±5 vs. 15±2.5, factor 8). No significant increases were seen for the Pol peptide in donor 3, or for either peptide in donor 4.

Example 2

Modification of the Amplispot Assay

Method

The Amplispot assay was carried out as described in Example 1, with the following modifications. Prior to overnight incubation with antigen, the responder cells (fresh or previously cryopreserved PBMC) were incubated for 45 minutes at 25° C. with 0 to 20 µl/well of 1 mg/ml monoclonal antibody to MHC class I (w6/32 without sodium azide, Cat. No. 16-9983, e-Bioscience, Inc.), or MHC class II (TU39 without sodium azide, Cat. No. RDI-HLA2-TU39XP, Research Diagnostics, Inc.). The antibody pre-incubation step was performed in a sterile 96-well round-bottom culture plate. Following pre-incubation, cells were transferred to the Amplispot plate to which cytokines (IL-7 and -15 at 1-5 ng/ml) and specific antigen are then added. The plate was incubated overnight (14-20 hours) at 37° C., 5% $CO_2$ and developed the following day as described (Jennes et al. (2002) *J. Immunol. Methods* 270:99-108).

Results

FIGS. 5A and 5B show the results of an Amplispot assay performed using MHC class I (A) or class II (B) blocking antibodies. Bars represent mean IFN-γ spot-forming cells (SFC) per million PBMC after subtracting background counts.

In (FIG. 5A), PBMC were stimulated with a minimal 9-mer peptide corresponding to the HLA-A*0201-restricted immunodominant epitope from cytomegalovirus (CMV) pp65 protein (495-503, NLVPMVATV; SEQ ID NO:01) in the absence of IL-7/15 (top panel), with 1 ng/ml IL-7/15 (center panel) or with 5 ng/ml IL-7/15 (lower panel). This minimal 9-mer peptide stimulates primarily CD8+ T-cell responses. MHC class I blocking antibody W6/32 (1 mg/ml) was added to duplicate wells in the amounts shown on the x-axis. IFN-γ production was inhibited by 27-42% in the presence of 2 µl W6/32, and by 58-71% in the presence of 10 µl W6/32.

In (FIG. 5B), PBMC were stimulated with a lysate of CMV-infected cells or a control lysate (Bio-Whittaker, Walkersville, Md.), which stimulates primarily CD4+ T-cell responses to CMV. The top panel shows responses in the absence of IL-7/15, and the lower panel shows responses in the presence of 5 ng/ml IL-7/15. MHC class II blocking antibody Tu39 (1 mg/ml) was added to duplicate wells in the amounts shown on the x-axis. In the absence of IL-7/15, IFN-γ production was quite low (55 SFC per $10^6$ PBMC), and was completely inhibited by 1 or 5 µl Tu39. In the presence of 5 ng/ml IL-7/15, IFN-γ production was increased by 3.3-fold. However, responses to CMV protein were inhibited by 46% in the presence of 1 µl Tu39, and by 66% in the presence of 5 µl Tu39.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of detecting an antigen-specific T lymphocyte in a sample, the method comprising:
   a) combining a cell sample comprising a T lymphocyte with an isolated antigen, an IL-15 receptor agonist, and an IL-7 receptor agonist, forming a test sample, wherein the IL-15 receptor agonist is naturally occurring IL-15, recombinant IL-15, or synthetic IL-15, and wherein the IL-7 receptor agonist is naturally occurring IL-7, recombinant IL-7, or synthetic IL-7; and
   b) detecting a T lymphocyte specific for the antigen in the test sample.

2. The method of claim 1, wherein the detecting step comprises detecting interferon-gamma (IFN-γ) secreted by the antigen-specific T lymphocyte.

3. The method of claim 1, wherein the IFN-γ is detected by capturing IFN-γ on a solid support, and detecting the captured IFN-γ with an antibody specific for IFN-γ.

4. The method of claim 1, wherein the antigen is an allergen.

5. The method of claim 1, wherein the antigen is an antigen associated with a pathogenic microorganism.

6. The method of claim 1, wherein the antigen is an autoantigen.

7. The method of claim 1, wherein the antigen is a tumor-associated antigen.

8. The method of claim 1, wherein the antigen-specific T lymphocyte is a CD4$^+$ T lymphocyte.

9. The method of claim 1, wherein the antigen-specific T lymphocyte is a CD8$^+$ T lymphocyte.

10. The method of claim 1, further comprising, in step (a), combining the cell sample with an antibody that binds a Class I MHC polypeptide, thereby reducing detection of CD8$^+$ T lymphocytes in the sample.

11. The method of claim 1, further comprising, in step (a), combining the cell sample with an antibody that binds a Class II MHC polypeptide, thereby reducing detection of CD4$^+$ T lymphocytes in the sample.

12. The method of claim 1, wherein the antigen is at least 80% pure.

13. The method of claim 1, wherein the antigen is synthetic.

* * * * *

UNITED STATES PATENT AND TRADEMARK OFFICE
CERTIFICATE OF CORRECTION

PATENT NO.         : 7,364,869 B2
APPLICATION NO. : 10/895239
DATED              : April 29, 2008
INVENTOR(S)     : Douglas Nixon et al.

Page 1 of 1

It is certified that error appears in the above-identified patent and that said Letters Patent is hereby corrected as shown below:

Please replace the Statement Regarding Federally Sponsored Research beginning on column 1, line 13, with the following revised statement:

STATEMENT REGARDING FEDERALLY SPONSORED RESEARCH

--The U.S. government has certain rights in this invention, pursuant to grant nos. R21-AI47746 and R01-AI46254 awarded by the National Institutes of Health.--

Signed and Sealed this

First Day of December, 2009

David J. Kappos
*Director of the United States Patent and Trademark Office*

SEQUENCE LISTING

```
<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: synthetic peptide

<400> SEQUENCE: 1

Asn Leu Val Pro Met Val Ala Thr Val
 1               5

<210> SEQ ID NO 2
<211> LENGTH: 9
<212> TYPE: PRT
<213> ORGANISM: Artificial Sequence
<220> FEATURE:
<223> OTHER INFORMATION: synthetic peptide

<400> SEQUENCE: 2

Ser Leu Tyr Asn Thr Val Ala Thr Leu
```

```
<210> SEQ ID NO 3
<211> LENGTH: 9
<212> TYPE: PRT
<213> ORGANISM: Artificial Sequence
<220> FEATURE:
<223> OTHER INFORMATION: synthetic peptide

<400> SEQUENCE: 3

His Pro Asp Ile Val Ile Tyr Gln Tyr
 1               5
```